US 6,589,229 B1

(12) United States Patent
Connelly et al.

(10) Patent No.: US 6,589,229 B1
(45) Date of Patent: Jul. 8, 2003

(54) WEARABLE, SELF-CONTAINED DRUG INFUSION DEVICE

(75) Inventors: Robert I. Connelly, Raleigh, NC (US); Charles D. Shermer, Raleigh, NC (US); Kenneth G. Powell, Raleigh, NC (US)

(73) Assignee: Becton, Dickinson and Company

( * ) Notice: Subject to any disclaimer, the term of this patent is extended or adjusted under 35 U.S.C. 154(b) by 107 days.

(21) Appl. No.: 09/629,977

(22) Filed: Jul. 31, 2000

(51) Int. Cl.[7] ............................................... A61K 9/22
(52) U.S. Cl. ..................... 604/890.1; 604/65; 604/66; 604/67
(58) Field of Search ................................ 604/21, 890.1, 604/65, 66, 67, 117, 132, 141, 138, 154, 156, 179; 600/561

(56) References Cited

U.S. PATENT DOCUMENTS

| 3,857,382 A | 12/1974 | Williams, Jr. et al. ...... 128/1 D |
| 3,963,380 A | 6/1976 | Thomas, Jr. et al. ........ 417/322 |
| 4,204,538 A | 5/1980 | Cannon .................. 128/214 R |

(List continued on next page.)

FOREIGN PATENT DOCUMENTS

| DE | 3320443 | 12/1984 |
| DE | 4320715 | 1/1995 |
| DE | 4332720 | 3/1995 |
| DE | 4402119 | 7/1995 |
| EP | 0400482 | 12/1990 |
| EP | 0603844 | 6/1994 |
| JP | 6138278 | 2/1986 |
| JP | 61123782 | 6/1986 |
| JP | 61171891 | 8/1986 |
| JP | 6383473 | 4/1988 |
| JP | 1285681 | 11/1989 |
| JP | 221080 | 1/1990 |
| JP | 2149778 | 6/1990 |
| JP | 2308988 | 12/1990 |
| WO | 9204569 | 3/1992 |
| WO | 9513838 | 5/1995 |
| WO | 9915820 | 4/1999 |

OTHER PUBLICATIONS

Bruce D. Wigness et al., "The Spring–Driven Implantable Pump: A Low–Cost Alternative", *ASAIO Journal 1992*, pp. M454–M457.
*Parade Magazine*, Nov. 28, 1999, p. 5.
P–803 Multilayer LVPZT Bender Actuators, Physik Instrumente (PI), Nano Positioning Catalog, p. 1.30 (1998).
General Specifications, Model No. QP21B Bimorph Actuator, Active Control eXperts, Inc. (1997).
ACX QuickPack Bimorph Actuator, Active Control eXperts, Inc. Website, http://acx.com/cool–picto.html (Sep. 21, 1999).
Bender Type Actuators (Bimorph and Multimorph Design), Physik Instrumente (PI), Nano Positioning Catalog, pp. 4.41–4.42 (1998).

(List continued on next page.)

*Primary Examiner*—Thomas Denion
*Assistant Examiner*—Jaime Corrigan
(74) *Attorney, Agent, or Firm*—Alan W. Fiedler

(57) ABSTRACT

A wearable, self contained drug infusion device is disclosed that is capable of achieving the precise flow rate control needed for dose-critical drugs such as insulin. In preferred embodiments of the device, piezoelectrically-actuated valve or pump structures are used in combination with thermal flow sensors and closed-loop control circuits for providing the desired flow rate control. The device has a two-part construction in which the more expensive electronic components are housed in a reusable portion and the fluid delivery components are housed in a separable disposable portion. The invention may also utilize a wireless unit for controlling the operation of the drug infusion device.

18 Claims, 20 Drawing Sheets

U.S. PATENT DOCUMENTS

| | | | |
|---|---|---|---|
| 4,207,871 A | 6/1980 | Jenkins | 128/214 R |
| 4,271,989 A | 6/1981 | O'Neill et al. | 222/282 |
| 4,274,407 A | 6/1981 | Scarlett | 128/213 |
| 4,326,517 A | 4/1982 | Whitney et al. | 128/214 F |
| 4,340,083 A | 7/1982 | Cummins | 137/499 |
| 4,344,743 A | 8/1982 | Bessman et al. | 417/317 |
| 4,492,360 A | 1/1985 | Lee, II et al. | 251/129 |
| 4,541,429 A | 9/1985 | Prosl et al. | 604/249 |
| 4,596,575 A | 6/1986 | Rosenberg et al. | 604/891 |
| 4,601,707 A | 7/1986 | Albisser et al. | 604/131 |
| 4,617,952 A | 10/1986 | Fujiwara et al. | 137/85 |
| 4,633,878 A | 1/1987 | Bombardieri | 128/635 |
| 4,669,660 A | 6/1987 | Weber et al. | 239/102.2 |
| 4,741,736 A | 5/1988 | Brown | 604/134 |
| 4,758,226 A | 7/1988 | Carre | 604/141 |
| 4,787,071 A | 11/1988 | Kreuter et al. | 367/140 |
| 4,842,017 A | 6/1989 | Reynolds | 137/601 |
| 4,886,499 A | 12/1989 | Cirelli et al. | 604/131 |
| 4,938,742 A | 7/1990 | Smits | 604/67 |
| 4,939,405 A | 7/1990 | Okuyama et al. | 310/330 |
| 4,944,659 A | 7/1990 | Labbe et al. | 417/322 |
| 4,998,918 A | 3/1991 | Mimura | 604/132 |
| 5,000,739 A | 3/1991 | Kulisz et al. | 604/132 |
| 5,012,835 A | 5/1991 | Ikehata et al. | 137/82 |
| 5,054,522 A | 10/1991 | Kowanz et al. | 137/625.33 |
| 5,085,562 A | 2/1992 | Van Lintel | 417/413 |
| 5,094,594 A | 3/1992 | Brennan | 417/322 |
| 5,096,643 A | 3/1992 | Kowanz et al. | 264/130 |
| 5,205,819 A | 4/1993 | Ross et al. | 604/67 |
| 5,262,696 A | 11/1993 | Culp | 310/328 |
| 5,267,589 A | 12/1993 | Watanabe | 137/625.65 |
| 5,271,724 A | 12/1993 | Van Lintel | 417/413 |
| 5,277,556 A | 1/1994 | Van Lintel | 417/413 |
| 5,327,041 A | 7/1994 | Culp | 310/328 |
| 5,336,062 A | 8/1994 | Richter | 417/413 |
| 5,354,032 A | 10/1994 | Sims et al. | 251/129.06 |
| 5,395,320 A | 3/1995 | Padda et al. | 604/65 |
| 5,415,629 A | 5/1995 | Henley | 604/20 |
| 5,542,821 A | 8/1996 | Dugan | 417/53 |
| 5,566,703 A | 10/1996 | Watanabe et al. | 137/1 |
| 5,569,187 A | 10/1996 | Kaiser | 604/67 |
| 5,611,676 A | 3/1997 | Ooumi et al. | 417/322 |
| 5,624,409 A | 4/1997 | Seale | 604/246 |
| 5,628,411 A | 5/1997 | Mills et al. | 209/644 |
| 5,643,207 A | 7/1997 | Rise | 604/93 |
| 5,681,152 A | 10/1997 | Ahs | 417/413.2 |
| 5,693,016 A | 12/1997 | Gumaste et al. | 604/131 |
| 5,698,485 A | 12/1997 | Brück et al. | 501/87 |
| 5,707,361 A | 1/1998 | Slettenmark | 604/131 |
| 5,759,015 A | 6/1998 | Van Lintel et al. | 417/322 |
| 5,779,218 A | 7/1998 | Kowanz | 251/129.06 |
| 5,810,325 A | 9/1998 | Carr | 251/30.02 |
| 5,836,750 A | 11/1998 | Cabuz | 417/322 |
| 5,840,062 A | 11/1998 | Gumaste et al. | 604/68 |
| 5,866,971 A | 2/1999 | Lazarus et al. | 310/328 |
| 5,899,218 A | 5/1999 | Dugan | 137/1 |
| 5,902,336 A | 5/1999 | Mishkin | 623/11 |
| 5,957,895 A | 9/1999 | Sage et al. | 604/181 |
| 5,970,998 A | 10/1999 | Talbot et al. | 137/1 |
| 5,984,894 A | 11/1999 | Poulsen et al. | 604/151 |
| 5,997,501 A * | 12/1999 | Gross et al. | 604/65 |
| 6,024,720 A * | 2/2000 | Chandler et al. | 604/35 |
| 6,033,191 A | 3/2000 | Kamper et al. | 417/322 |
| 6,074,369 A | 6/2000 | Sage et al. | 604/181 |

OTHER PUBLICATIONS

"Using the QuickPack Actuator as a Bimorph", QuickNOTE QN–02, Active Control eXperts (1997).

"Attaching the QuickPack Transducer to a Structure with Epoxy", QuickNOTE QN–01, Active Control eXperts, Inc. (1997).

"ACX Introduces Standard Line of Piezoelectric Bimorph Actuators", Press Release, Active Control eXperts, Inc. (Dec. 1, 1997).

"ACX Awarded Manufacturing Contract With Landis & Staefa to Supply Piezoelectric Actuators for Pneumatic Valves", Press Release, Active Control eXperts, Inc. (Dec. 3, 1996).

"The IMM–Micropump", MesoSystems Technology, Inc. (Nov. 1997).

M. Niggemann et al., "Fabrication of Miniaturized Biotechnical Devices", Institut für Mikrotechnik Mainz (IMM) GmbH (1998).

Usage Instructions, ULA Controller for IMM Membrane Micropump, Institut für Mikrotechnik Mainz GmbH (1998).

* cited by examiner

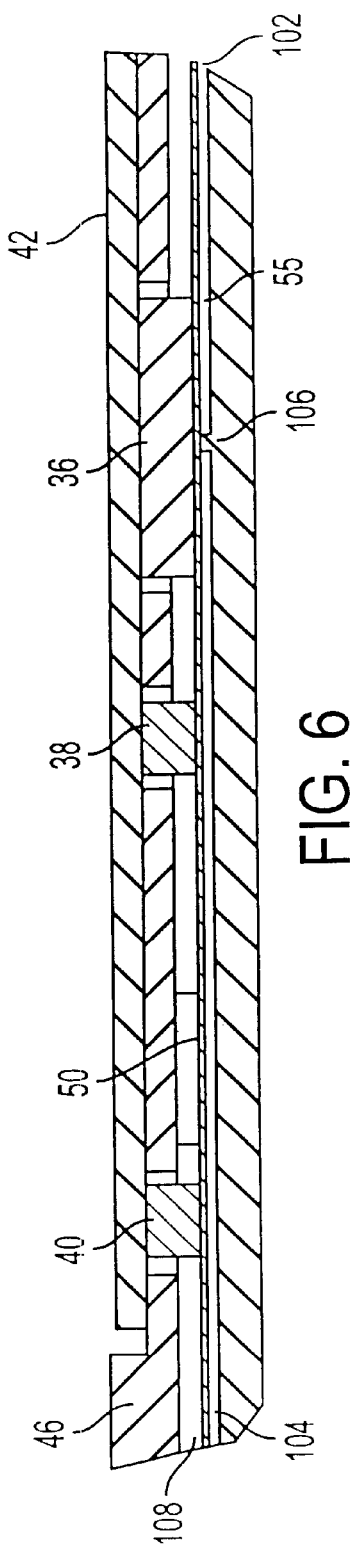
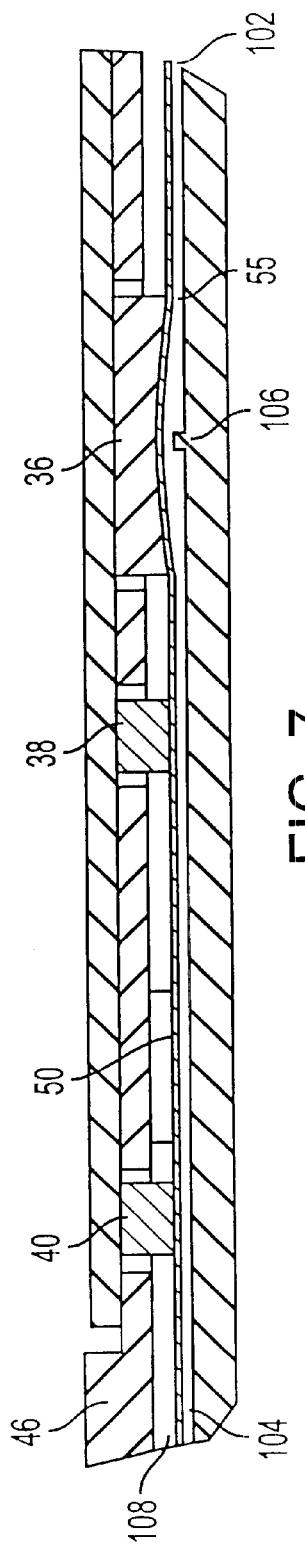
FIG. 6
FIG. 7

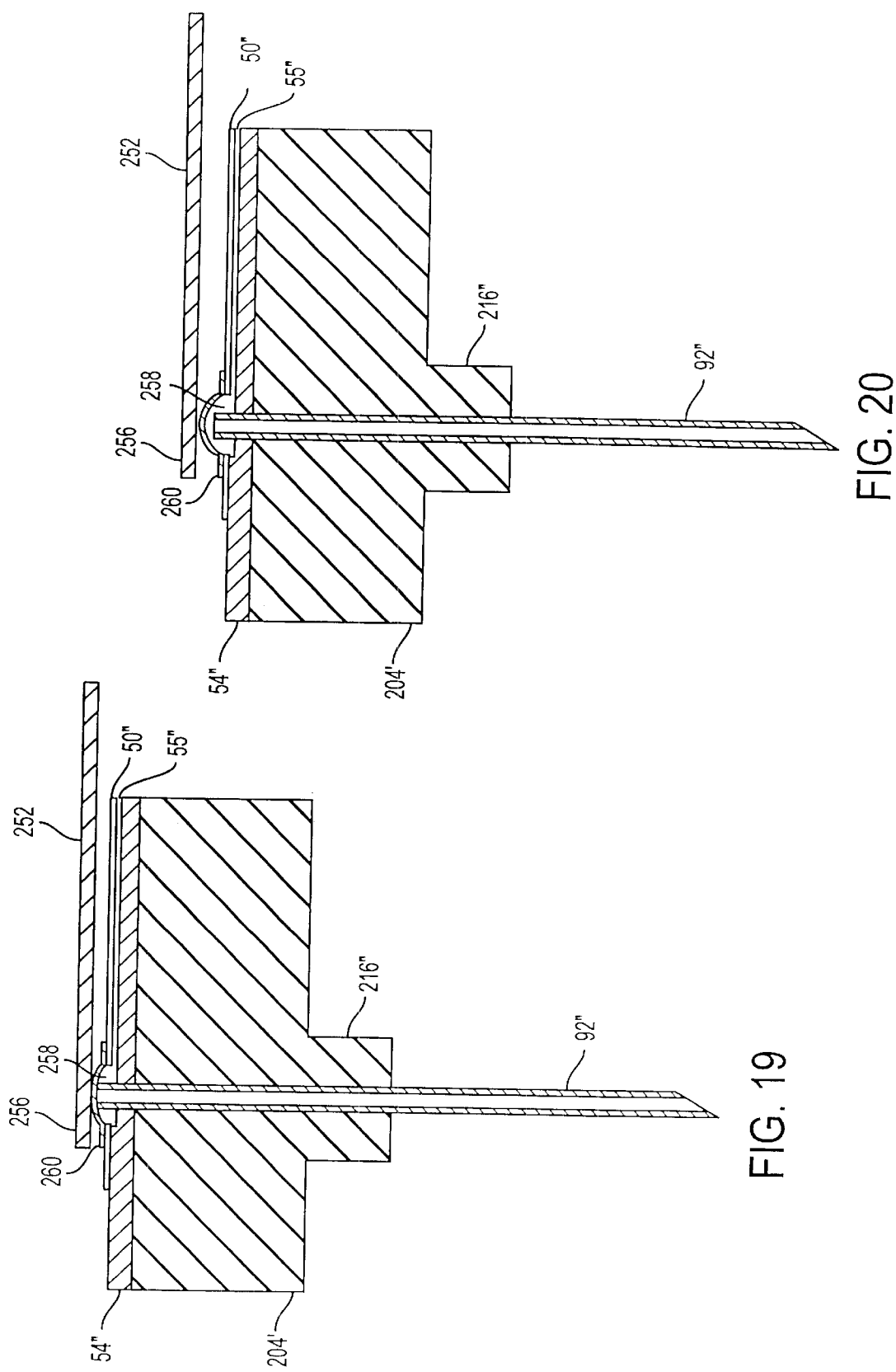

WEARABLE, SELF-CONTAINED DRUG INFUSION DEVICE

FIELD OF THE INVENTION

The present invention relates generally to fluid delivery devices, and is particularly concerned with a wearable, self-contained drug infusion device that can be used to deliver a variety of medications, including but not limited to insulin, to a patient.

BACKGROUND OF THE INVENTION

Diabetes is a chronic disease that is caused by both hereditary and environmental factors. It is characterized by the body's inability to control glucose levels. Left untreated, it causes damage to the circulatory and nervous systems and results in organ failures, amputations, neuropathy, blindness and eventually death. It has been definitively shown that the cost of the complications related to diabetes significantly exceeds the cost of therapy. The Diabetes Control and Complications Trial (DCCT) was a ten-year study of 1400 patients to assess the benefits of close control of blood glucose levels. The study found that such close control provided 50% to 75% reductions in retinopathy, nephropathy, neuropathy and cardiovascular risk.

There are roughly 17.5 million people with diabetes in the United States and Europe, and about 60 million more worldwide. Roughly 35% of these people use insulin to maintain close control of their glucose levels. Proper control of blood glucose levels through programmed insulin injection or infusion allows a high quality of life and a life expectancy of an additional 35 to 40 years from diagnosis.

Currently, there are two principal modes of daily insulin therapy. The first mode includes syringes and insulin pens. These devices are simple to use and are relatively low in cost, but they require a needle stick at each injection, typically three to four times per day. The second is infusion pump therapy, which entails the purchase of an expensive pump that lasts for about three years. The initial cost of the pump is a high barrier to this type of therapy. From a user perspective, however, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer glucose control and an improved feeling of wellness.

The typical patient on intensive therapy injects insulin to provide a basal level and then takes supplemental boluses prior to meals during the day. Those on infusion pumps program their pumps to mimic this type of delivery schedule. There are several existing or anticipated means of insulin therapy that a patient might consider.

The first are so-called oral agents that enhance the ability of the body to utilize insulin. Typical compounds include sulfonylureas, biguanides and thiazolidinediones. Oral agents are initially appropriate for Type 2 diabetics, whose bodies produce some insulin, although after a period of years these patients generally need to supplement with additional insulin. For Type 1 diabetics, the body does not produce insulin and these agents are not effective.

Once the oral agents are no longer effective, insulin is injected using syringes or multi-dose insulin pens. The syringe is the least expensive means of delivery, but many patients are willing to pay a premium for the convenience of the insulin pen.

A recent advance has been the development of extremely long-acting insulins. While regular insulins have a physiological onset in 10 minutes and peak activity in about 90 minutes, current long-acting insulins peak in roughly 8 hours. This type of insulin can be taken in the morning and can be accompanied by bolus delivery at meals. The alternative of simply taking all of one's insulin requirement in basal delivery is believed by many to be therapeutically unsound. Insulin resistance is theorized to build as a result of high concentrations of insulin in the bloodstream, and as a result ever increasing amounts of insulin are necessary to control blood glucose levels. Unfortunately, the basal plus bolus profile still results in the same high and undesirable frequency of injections, typically four per day. Long-acting insulin does provide good therapy for those patients whose bodies benefit from supplemental basal insulin, but this is a temporary condition and simply delays a more rigorous insulin injection regimen for six months to two years.

As their interest in intensive therapy increases, users typically look to insulin pumps. However, in addition to their high cost (roughly 8 to 10 times the daily cost of syringe therapy) and limited lifetime, insulin pumps represent relatively old technology and are cumbersome to use. Also, from a lifestyle standpoint, the tubing (known as the "infusion set") that links the pump with the delivery site on the user's abdomen is very inconvenient and the pumps are relatively heavy, making carrying the pump a bother.

A new method of insulin delivery currently undergoing development is pulmonary delivery. The principal issue with pulmonary delivery is criticality of dose, as pulmonary delivery is relatively inefficient and difficult to quantify. As a result, it will be difficult to keep blood glucose levels in control with this delivery form, although it may prove very useful as a supplement for bolus delivery at mealtime. The inefficiency of delivery (currently about 10%) significantly drives up the cost of pulmonary therapy. The implications of chronic inhalation of insulin are also unknown.

In summary, patients on oral agents eventually move to insulin, and existing pump therapy is very expensive. Interest in better therapy is on the rise,,accounting for the observed growth in pump therapy and increased number of daily injections. What is needed to fully meet this increased interest is a form of insulin delivery that combines the best features of daily injection therapy (low cost and ease of use) with those of the insulin pump (continuous infusion, precision dosing and programmable delivery schedules), and that avoids the disadvantages of each. This will allow a greater number of patients to have access to improved insulin therapy at lower cost.

Several attempts have been made to provide ambulatory or "wearable" drug infusion devices that are low in cost and convenient to use. Some of these devices are intended to be partially or entirely disposable. In theory, devices of this type can provide many of the advantages of an infusion pump without the attendant cost and inconvenience. Unfortunately, however, many of these devices cannot provide precise control over the flow rate of the drug at a low delivery cost, and are thus not compatible with dose-critical drugs such as insulin. In addition, devices that operate with fixed insulin flow rates may meet cost targets but still require bolus injections at mealtimes. Ultimately, therefore, these existing devices do not represent an optimal alternative to infusion pumps.

SUMMARY OF THE INVENTION

In accordance with the present invention, the disadvantages and limitations of the prior art are substantially avoided by providing a wearable, self-contained drug infusion device that is capable of achieving the precise flow rate control needed for dose-critical drugs such as insulin. In preferred embodiments of the invention, piezoelectrically-actuated valve or pump structures are used in combination with thermal flow sensors and closed-loop control circuits for providing the desired flow rate control. The miniaturization that is possible with each of these technologies allows the drug infusion device to have very small dimensions so that it can be worn by the user with a minimum of discomfort and inconvenience, while at the same time allowing for the close control over flow rate that is required for safe and effective delivery of insulin and other drugs. Preferred embodiments of the device have a two-part construction in which the more expensive electronic components are housed in a reusable portion and the fluid delivery components are housed in a separable disposable portion. This is advantageous not only in reducing the effective cost of the device to the user, but also in assuring sterility of the drug and preventing fluid contamination of the reusable portion by confining the fluid flow path to the disposable portion. Also, because control over the flow rate of the drug is carried out electronically, variable and/or programmable control over the flow rate is possible. This renders the device particularly suitable for those drugs (such as insulin) that require different delivery rates at different times for different patients.

In accordance with the first embodiment of the present invention, a wearable, self-contained device for delivering a liquid medication by continuous infusion into a patient comprises a disposable portion and a reusable portion that is removably connected to the disposable portion. The disposable portion comprises a housing, a reservoir in the housing for containing a supply of the liquid medication and for delivering the liquid medication under pressure, and a delivery cannula carried by the housing. A flow channel conducts the liquid medication from the reservoir to the delivery cannula. The reusable portion comprises a closed loop control circuit for maintaining a predetermined flow of liquid medication through the flow channel of the disposable portion. The infusion device also includes a flow control valve in at least one of the disposable and reusable portions for controlling the flow of liquid medication through the flow channel from the reservoir to the delivery cannula; an actuator in at least one of the disposable and reusable portions for actuating the flow control valve, the actuator being electrically connectable to the closed loop control circuit of the reusable portion; and a flow sensor in at least one of the disposable and reusable portions for sensing the flow of liquid medication through the flow channel of the disposable portion, the flow sensor being electrically connectable to the closed loop control circuit of the reusable portion.

In a particularly preferred implementation of the first embodiment of the invention, the reservoir comprises at least one Belleville spring element for pressurizing the liquid medication contained in the reservoir. In this embodiment, the flow control valve may comprise a fixed obstruction in the flow channel and a flexible membrane that is held in contact with the obstruction by the actuator, with such contact preventing liquid flow through the flow channel except when the actuator is energized by the control circuit. The actuator preferably comprises a piezoelectric element which, when energized by the control circuit, flexes to allow the membrane to separate from the obstruction so that the liquid medication can flow through the flow channel. The piezoelectric element is preferably energized in a pulsatile manner by the control circuit, so that the flow control valve is repeatedly opened and closed with a duty cycle that maintains a predetermined average flow rate of the liquid medication through the flow channel. The flow sensor preferably comprises a thermal emitter and a thermal detector, both of which are in thermal contact with the liquid medication flowing in the flow channel, with the thermal emitter being located upstream of the thermal detector relative to the direction of liquid flow in the flow channel. Preferably, at least one wall of the flow channel comprises a flexible membrane which forms an exposed face of the disposable portion that is brought into contact with the reusable portion when the disposable and reusable portions are connected together. In this embodiment, the actuator and flow sensor may be contained in the reusable portion and may operate through the flexible membrane of the disposable portion, so that the flow channel can remain sealed when the reusable portion is disconnected from the disposable portion.

In accordance with a second embodiment of the present invention, a wearable, self-contained device for delivering a liquid medication by continuous infusion into the skin of a patient is provided that is similar in overall construction to the embodiment described previously, except that the reservoir in the disposable portion is not required to deliver the liquid medication under pressure. The disposable portion of the device comprises the housing, a reservoir in the housing for containing a supply of the liquid medication, a delivery cannula carried by the housing, and a flow channel for conducting the liquid medication from the reservoir to the delivery cannula. As in the previously-described embodiment, a reusable portion of the device is removably connected to the disposable portion, and includes a closed loop control circuit for maintaining a predetermined flow of liquid medication through the flow channel of the disposable portion. In this embodiment, however, the infusion device further includes a pump in at least one of the disposable and reusable portions for pumping the liquid medication through the flow channel from the reservoir to the delivery cannula, the pump being electrically connectable to the closed loop control circuit; and a flow sensor in at least one of the disposable and reusable portions for sensing the flow of liquid medication through the flow channel, the flow sensor being electrically connectable to the closed loop control circuit.

In a particularly preferred implementation of an infusion device in accordance with the second embodiment of the invention, the pump is contained in the disposable portion and comprises a diaphragm pump that is driven by an actuator in at least one of the disposable and reusable portions. The actuator preferably comprises a piezoelectric element, which may be of the conventional disk type or of the cantilevered type. The diaphragm pump preferably comprises one or more check valves for restricting the flow of liquid medication to a single direction. As in the previously-described embodiment, the flow sensor preferably comprises a thermal emitter and a thermal detector, both of which are in thermal contact with the liquid medication flowing in the flow channel, with the thermal emitter being located upstream of the thermal detector relative to the direction of liquid flow in the flow channel. Preferably, at least one wall of the flow channel comprises a flexible membrane which forms an exposed face of the disposable portion that is brought into contact with the reusable portion when the disposable and reusable portions are connected together. In this embodiment, the flow sensor may be contained in the reusable portion and may operate through the flexible membrane of the disposable portion, so that the flow channel can remain sealed when the reusable portion is disconnected from the disposable portion.

In accordance with a further aspect of the present invention, a system for delivering a liquid medication by continuous infusion into or through the skin of a patient may comprise three separate components. The first component is a disposable portion comprising a housing, a reservoir in the housing for containing a supply of the liquid medication, a delivery cannula carried by the housing, and a flow channel for conducting the liquid medication from the reservoir to the delivery cannula. The second component is a reusable portion that is removably connectable to the disposable portion. The reusable portion contains electrical flow control circuitry for controlling the flow of liquid medication in the flow channel of the disposable portion in response to wireless control signals. The reusable and disposable portions, when connected to each other, constitute a wearable, self-contained infusion device. The third component is a wireless unit that is separate from the usable and disposable portions. The wireless unit transmits wireless control signals to the reusable portion to control the flow of liquid medication in the flow channel of the disposable portion.

In particularly preferred embodiments of a liquid medication delivery system in accordance with this aspect of the present invention, the wireless unit transmits either radio frequency or optical (e.g., infrared) signals to the reusable portion. The wireless unit preferably includes a keypad and a display device, and may also receive and display status information that is transmitted by the reusable portion. Examples of status information may include a flow rate of the liquid medication, an amount of time remaining until the reservoir in the disposable portion becomes empty, a quantity of liquid medication remaining in the reservoir of the disposable portion, a warning to the user that the flow rate of liquid medication in the disposable portion is incorrect, and an indication of a battery condition in the reusable portion.

BRIEF DESCRIPTION OF THE DRAWINGS

The various objects, advantages and novel features of the present invention will be more readily understood from the following detailed description when read in conjunction with the appended drawings, in which:

FIG. 6 is a magnified cross-sectional view of a portion of the circled area in FIG. 5, showing the fluid flow path as it appears when the piezoelectric element is de-energized;

FIG. 7 is a magnified cross-sectional view similar to that of FIG. 6, showing the fluid flow path as it appears when the piezoelectric element is energized;

FIGS. 19 and 20 are cross-sectional views taken longitudinally through the outlet end of the liquid flow channel and through the delivery cannula in the embodiment of FIG. 18;

Throughout the drawings, like reference numerals will be understood to refer to like parts and components.

DETAILED DESCRIPTION OF THE PREFERRED EMBODIMENTS

Figure 1:
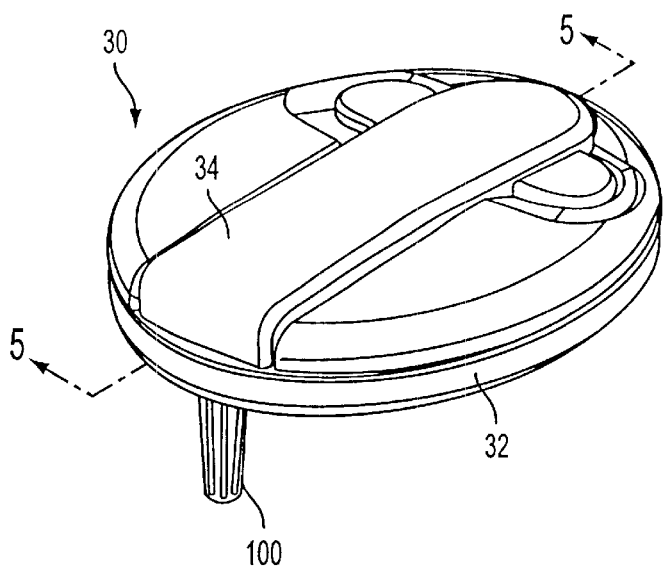
FIG. 1 is a perspective view of a fully assembled drug infusion device constructed in accordance with a first embodiment of the present invention.
Figure 2:
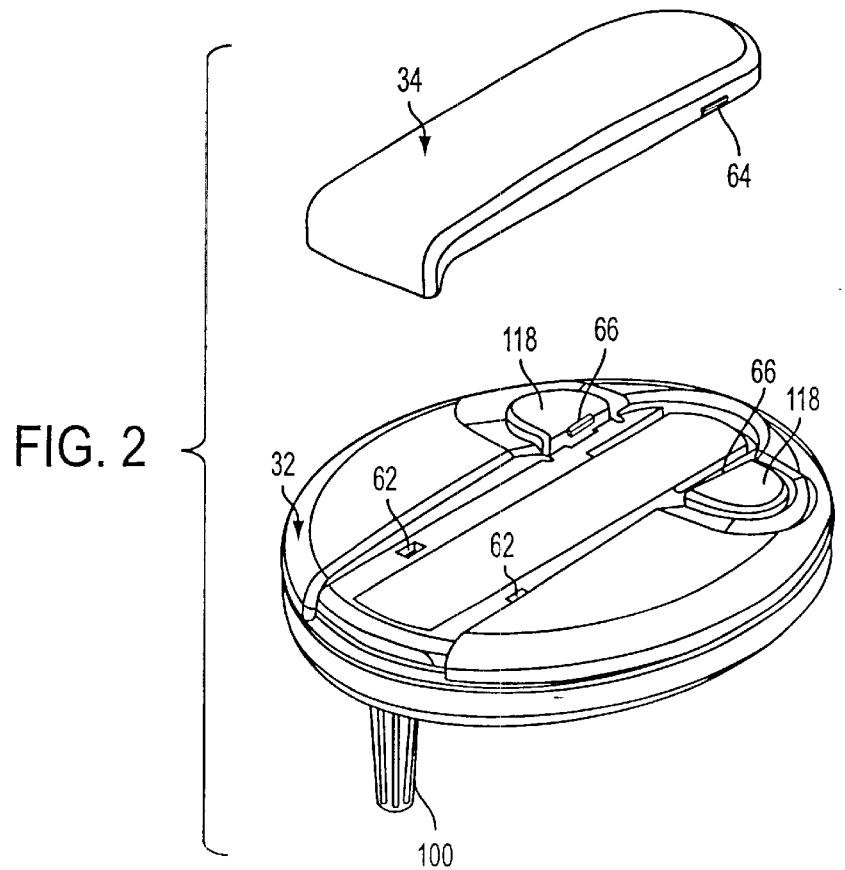
FIG. 2 is a partially exploded perspective view of the drug infusion device shown in FIG. 1, with the reusable portion of the device shown removed from the disposable portion of the device.

A first embodiment of a drug infusion device 30 constructed in accordance with the present invention is illustrated in FIGS. 1 and 2. The device 30 may be used for the delivery of a liquid medication, preferably but not necessarily insulin, by continuous infusion into or through the skin of a patient. The device 30 is intended to be worn on the surface of the skin by the user, with a cannula (hollow needle) penetrating into the user's skin or transcutaneously through the skin into the subcutaneous tissue. Its design is preferably such that the flow rate profile of the liquid medication is fully programmable and can be altered throughout the course of a day by the wearer. Although the present invention is not limited to specific dimensions, the device 30 preferably has an overall size (excluding the delivery cannula and the cannula shield 100) of about 65 millimeters in length, 50 millimeters in width, and 12 millimeters in height. The delivery cannula may be rigid or flexible and may have any desired length, but a typical length is between 5 millimeters and 12 millimeters. The cannula shield 100 may be about 15 millimeters in height, making the total height of the device 30 about 27 millimeters. In lieu of a single delivery cannula, a plurality of microneedles may be used to deliver the liquid medication to the skin of the user. Since a typical microneedle length is only 0.5 millimeter, a device 30 constructed using microneedles may have a height dimension not much greater than 12 millimeters. The term "delivery cannula" as used herein will be understood to include not only a hollow needle of the type shown in the drawings, but also one or more microneedles or other structures that deliver liquid medications into or through the skin, whether by skin penetration or otherwise.

The device 30 includes a disposable portion 32 which contains the medicament reservoir, delivery cannula, skin adhesive and complete liquid flow path, as well as a removable reusable portion 34 containing a battery, logic controller chip, piezoelectric valve actuator, and flow sensor. The reusable portion 34 snaps into place on the disposable portion 32, as shown in FIGS. 1 and 2, without the need for special alignment or interconnections for fluid flow paths. With this configuration, the user can dispose of the disposable portion every one to three days, whenever its internal medicament reservoir is empty, and can snap the reusable portion 34 onto a new disposable portion 32 for convenient disease management. The reusable portion 34 may be replaced after about 30 days, or may be used indefinitely if its internal battery is replaceable or rechargeable.

A desirable feature of the device 30 involves the relationship between the disposable portion 32 and the reusable portion 34. It is desired by the user that the connection be reliable, that it not leak, that it is sterile, that it is easy to perform, and that the reusable portion 34 does not become contaminated with the medicament such that its performance may be affected. To this end, the drug infusion device 30 utilizes a connection in which the liquid medicament is never in contact with the reusable component 34. As will be described in detail hereinafter, the liquid flow in the disposable portion 32 is directed to a thin channel on its outside surface, and a thin membrane is sealed over the channel to serve as one wall of the liquid flow path. The reusable portion 34 of the device 30 performs flow sensing and flow control functions across this membrane without coming into direct contact with the liquid medicament.

As will be described, the delivery concept embodied in the embodiment of FIGS. 1 and 2 is that of a pressurized reservoir with a flow path leading to the cannula that penetrates into or through the skin of the wearer. To control the flow rate, a conventional disk-type piezoelectric element is pressed against the membrane, nominally sealing off the flow path until a voltage is applied to the piezoelectric element. The voltage causes the piezoelectric element to bow or deflect away from the pinched-off flow path, thereby allowing the liquid medicament to pass into the delivery needle. By repeatedly applying and removing the voltage from the piezoelectric element, the device acts in a pulsatile manner to control the delivery rate of the liquid medicament. The duty cycle of the piezoelectric element (that is, the ratio of its "on" time to its "off" time) determines the effective flow rate of the liquid medicament over time.

For precise flow rate control, closed-loop operation of the drive circuit for the piezoelectric element is desired. To allow for a closed-looped operation, a flow sensor is used to feed back information to the controller as to what flow rate is actually being produced by a given modulation of the piezoelectric element. In the preferred embodiment, flow sensing is carried out by means of a "thermal signature". Two stations along the flow path are separated from one another by a small distance. A small, electronically-controlled heating element is located at the upstream station, and a small thermal sensor is located at the downstream station. To measure the flow rate of the liquid medicament, the following steps occur: (1) the piezoelectric element opens to its full "on" state to allow the liquid medicament to flow at the maximum rate afforded by the current pressure in the reservoir; (2) the heating element is then energized momentarily to "inject" a pulse of heat through the membrane and into the liquid flow path, and a timer is started; and (3) when the element of fluid into which the heat was injected reaches the downstream thermal sensor, the timer is stopped and the piezoelectric element is closed. Since the distance between the heating and sensing stations is known, and since the cross-sectional area of the liquid flow path is also known, a volumetric flow rate can be calculated based on the timer value in step (3). In the preferred embodiment, the liquid medicament reservoir is pressurized by two Belleville springs which are designed to provide a very nearly constant pressure over the entire range from full to empty. As a result, the deviation of the actual full "on" flow rate—that is, the liquid flow rate that occurs when the piezoelectric element is fully opened—from its nominal value is likely to be small. Therefore, the flow sensor is required to operate in only a small dynamic range to occasionally calibrate the controller to the actual pressure in the reservoir at the time in question.

Another feature of the device 30 shown in FIGS. 1 and 2, to be described in more detail hereinafter, is the "fail safe" manner in which the flow of liquid medicament is started when the reusable portion 34 is snapped onto the disposable portion 32. When the disposable portion 32 is initially provided to the user, it is preferably prefilled with the desired medicament. This allows the pressurized reservoir to be hermetically sealed from environmental exposure or leakage. When the reusable portion 34 is snapped into place, a resiliently-mounted protrusion on the top cover of the disposable portion 32, which carries a small "start" cannula, is deflected downwardly until the start cannula punctures a protuberance at the edge of the reservoir, which contains an elastomeric sealing material. When this occurs, the start cannula penetrates the reservoir and conducts the pressurized liquid medicament into the main flow path of the drug infusion device 30, and the elastomeric member maintains the start cannula sealed and free of leaks. The mechanical timing of the interconnection also ensures that the piezoelectric element is in place and properly seated to pinch off the flow channel before the start cannula initiates the flow from the reservoir. In a similar fashion, if the reusable portion 34 is removed during operation the device 30, the start cannula withdraws from the reservoir and stops the flow before the piezoelectric element can move to its open position.

Figure 3:
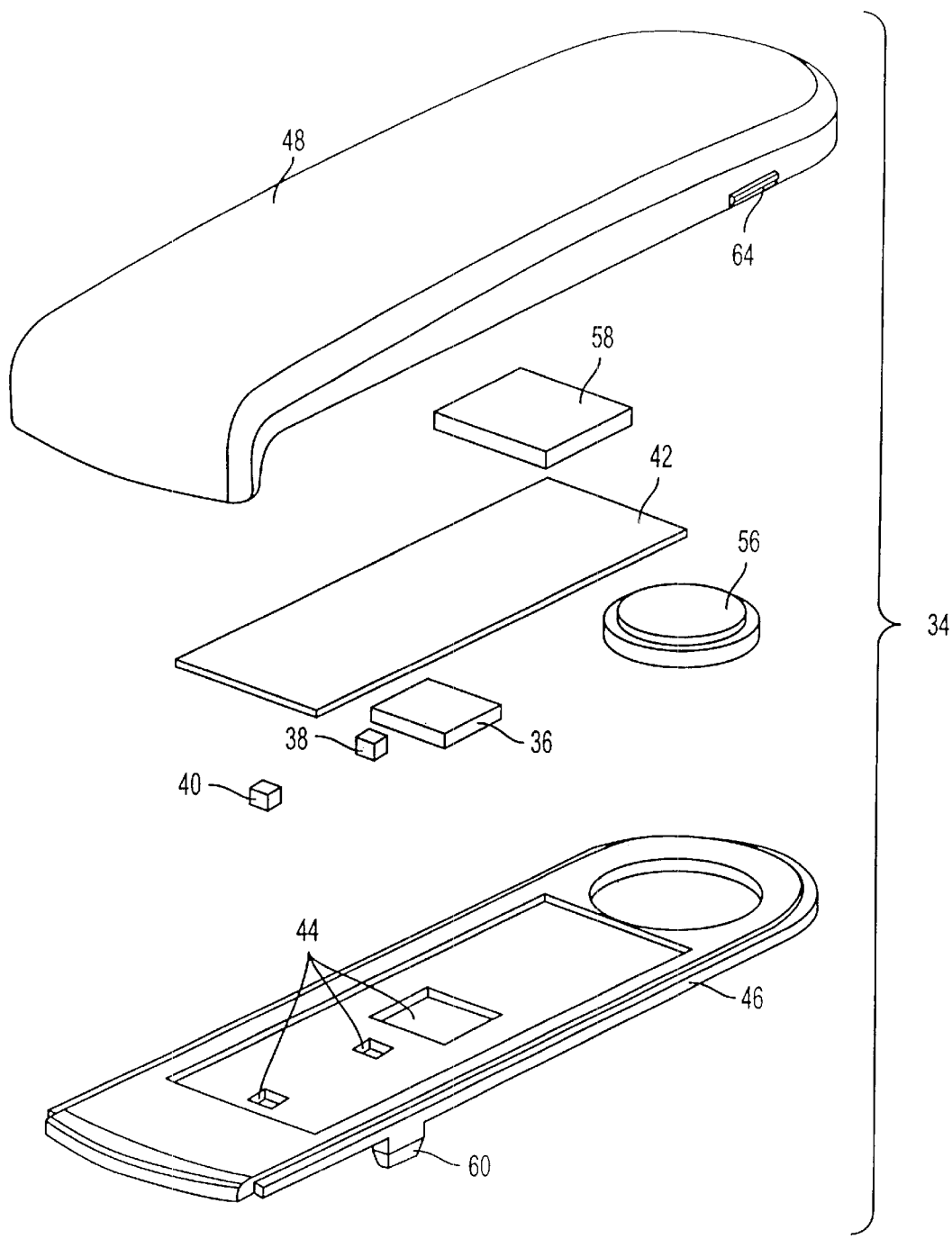
FIG. 3 is an enlarged, exploded perspective view illustrating the internal components of the reusable portion of the drug infusion device shown in FIGS. 1 and 2.

Further details of the drug infusion device 30 of FIGS. 1 and 2 will now be described in connection with FIGS. 3–11. Referring first to FIG. 3, the reusable portion 34 of the device 30 is shown in an exploded view. A disk-type piezoelectric element 36, as well as a thermal emitter 38 and thermal detector 40, are mounted on the bottom of a circuit board 42 so that they are exposed through holes 44 in a bottom cover 46 of the reusable portion 34. The bottom cover 46 and a mating top cover 48, which are both preferably made of plastic materials, form a housing for the reusable portion 34 of the device 30. The piezoelectric element 36, thermal emitter 38 and thermal detector 40 extend slightly beyond the bottom surface of the bottom cover 46. In this manner, the piezoelectric element 36, thermal emitter 38 and thermal detector 40 are placed into intimate and forced contact with the top surface of a membrane 50 (visible in FIG. 4) covering a recessed flow path area 52 formed in a plastic top cover 54 of the disposable portion 32. This forced contact allows the piezoelectric element 36 to seal off a flow channel 55 in the flow path area 52 until the piezoelectric element 36 is energized to allow the liquid medication in the disposable portion 32 to flow toward the delivery needle. In addition, the forced contact provides a short thermal conduction path so that the thermal emitter 38 and thermal detector 40 can operate effectively. A further advantage of the forced contact is that it takes up tolerances in the assembled components, so that the manufacturing will be more robust.

Additional components in the reusable portion 34 of the device 30 include a coin-type battery 56 and a logic controller chip 58. The logic controller chip 58 controls the piezoelectric element 36 in response to inputs received from the flow sensor comprising the thermal emitter 38 and thermal detector 40. In this way, the logic controller chip 58 regulates the flow rate of the liquid medication through the flow path channel 55 of the disposable portion 32. A second function of the logic controller chip 58 is to provide wireless, two-way radio frequency (RF) or infrared (IR) communication with an external programming unit. The external programming unit is not shown in FIG. 3, but will be described in detail below in connection with FIGS. 20 and 21. It will be understood that the circuit board 42 includes suitable electrically conductive paths (not shown) for interconnecting the piezoelectric element 36, thermal emitter 38, thermal sensor 40, battery 56 and logic controller 58.

To assist the user in locating and seating the reusable portion 34 on top of the disposable portion 32, a tab 60 is provided on each side of the bottom cover 46 of the reusable portion 34. One of these tabs is indicated at 60 in FIG. 3. The tabs 60 serve to locate and center the reusable portion 34 over the flow path area 52 of the disposable portion 32. The tabs 60 are received in holes 62 (visible in FIGS. 2 and 4) located on either side of the flow path area 52. This arrangement also serves to enhance the effectiveness of the thermal emitter 38 and thermal sensor 40 which constitute the flow sensor of the reusable portion 34. Two tabs 64 on opposite sides of the top cover 48 of the reusable portion 34 snap into mating tabs 66 on the top cover 54 of the disposable portion 32 during assembly by the user, thereby securing the reusable portion 34 to the disposable portion 32.

Figure 4:
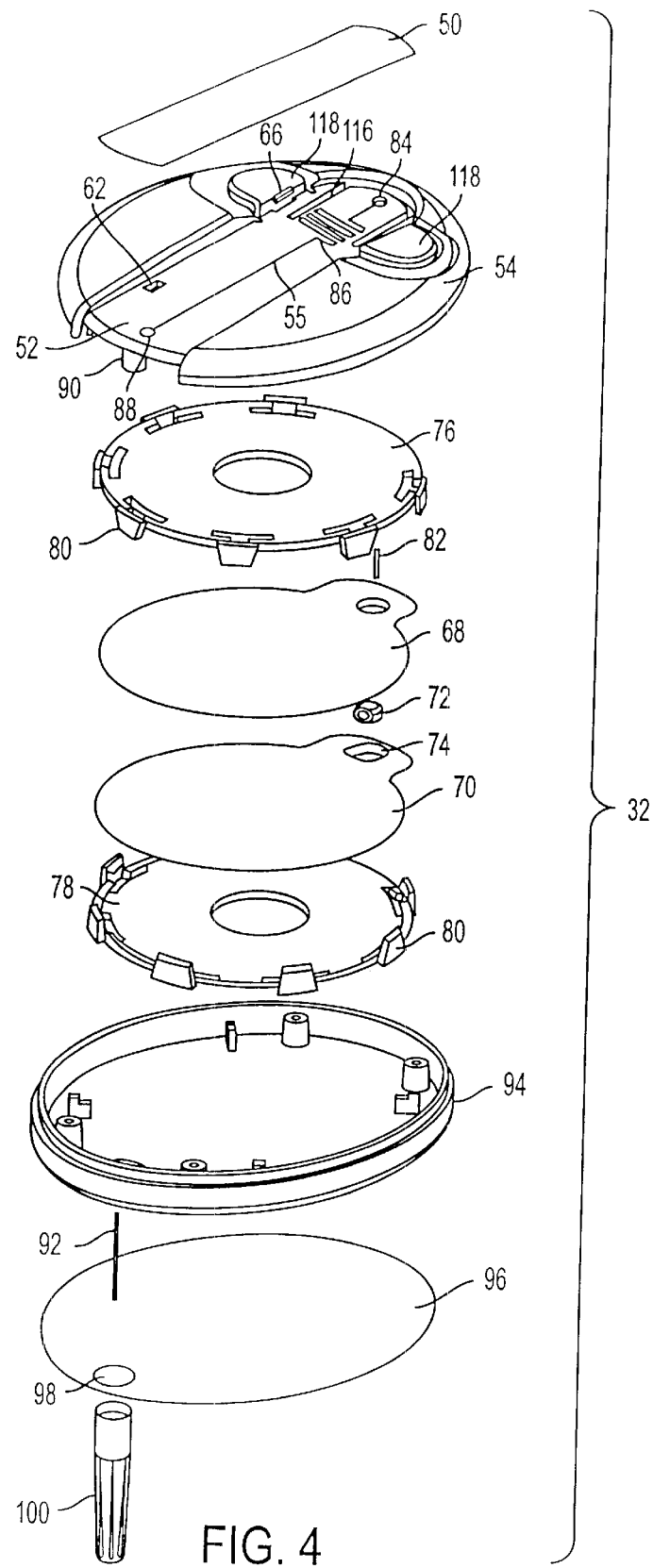
FIG. 4 is an exploded view of the disposable portion of the drug infusion device shown in FIGS. 1 and 2.

FIG. 4 is an exploded view of the disposable portion 32 of the drug infusion device 30 of FIG. 1. A pressurized reservoir for the liquid medication is formed by two membranes 68 and 70 which are heat-sealed together around their edges. Before the membranes 68 and 70 are sealed together, a septum seal piece 72 is dropped into a thermoformed pocket 74 in the lower membrane 70. The septum 72 acts as a self-sealing puncture location for starting the flow of liquid medication, as will be described hereinafter. The sealed bladder formed by the two membranes 68 and 70 is trapped between two identical Belleville spring disks 76 and 78, which are attached to one another by snaps 80 located around their peripheral edges. Due to the inward-pointing conical shape of the Belleville spring disks 76 and 78, the bladder formed by the heat-sealed membranes 68 and 70 is maintained under relatively constant pressure regardless of whether it is full or empty. Further details concerning the use of Belleville spring disks in a fluid reservoir can be found in commonly-assigned U.S. Pat. Nos. 5,957,895 and 6,074,369, both issued to Burton H. Sage and Robert I. Connelly, which are expressly incorporated herein by reference.

The flow path of the liquid medication in FIG. 4 begins with a start cannula 82. The start cannula 82 is hubbed into a protrusion on the inside (lower) surface of the top cover 54 of the disposable portion 32, just below an inlet 84 to the flow channel 55 that is formed in the outside (top) surface of the top cover 54 near one end of the flow path area 52. The liquid medication then flows through the flow channel 55 to an outlet 88 located above a delivery cannula hub 90. The flow channel 55 is preferably square in cross-section, with a width of about 0.01 inch and a height of about 0.01 inch. A serpentine region 86 of the flow channel 55 serves as a flow resistor to limit the maximum flow rate of the liquid medication through the flow channel 55 during the "on" times of the piezoelectric element 36. A rigid (e.g., stainless steel) or flexible delivery cannula 92 is hubbed into the cannula hub 90, completing the flow path into or through the skin of the user. To provide the fourth wall of the square flow channel 55 on the top surface of the top cover 54, the membrane 50 is sealed over the entire flow path area 52 by means of an adhesive, heat-sealing or any other suitable method. The membrane 50 is sufficiently thin, flexible and thermally conductive to allow the piezoelectric element 36, thermal emitter 38 and thermal detector 40 of FIG. 3 to perform their required functions. The membrane 50 may consist of any suitable material, but a preferred material is polycarbonate having a thickness of about 2 to 3 mils.

The reservoir assembly (consisting of the membranes 68 and 70 and the Belleville spring disks 76 and 78) is snapped onto a plastic bottom cover 94 and enclosed by the top cover 54 to complete the assembly of the disposable portion 32 of the drug infusion device 30. A liner 96 with adhesive layers on both sides is used to adhere the device 30 to the skin of the user during at least a 24-hour period. The delivery cannula 92 passes through a hole 98 in the liner 96. A cannula shield 100 is pushed onto the delivery cannula hub 90 to protect the delivery cannula 92 prior to use of the device 30.

In alternative embodiments of the invention, the fixed delivery cannula 92 can be replaced by an extendible and/or retractable delivery cannula as shown, for example, in the aforementioned U.S. Pat. Nos. 5,957,895 and 6,074,369. Prior to use of the device 30, the delivery cannula can be held in a retracted position within the device 30. Following attachment of the device 30 to the user's skin, the delivery cannula can be manually or automatically extended so that it penetrates into or through the user's skin. After removal of the device 30 from the user's skin, the delivery cannula can be retracted once again so that the device 30 can be disposed of safely.

Figure 5:
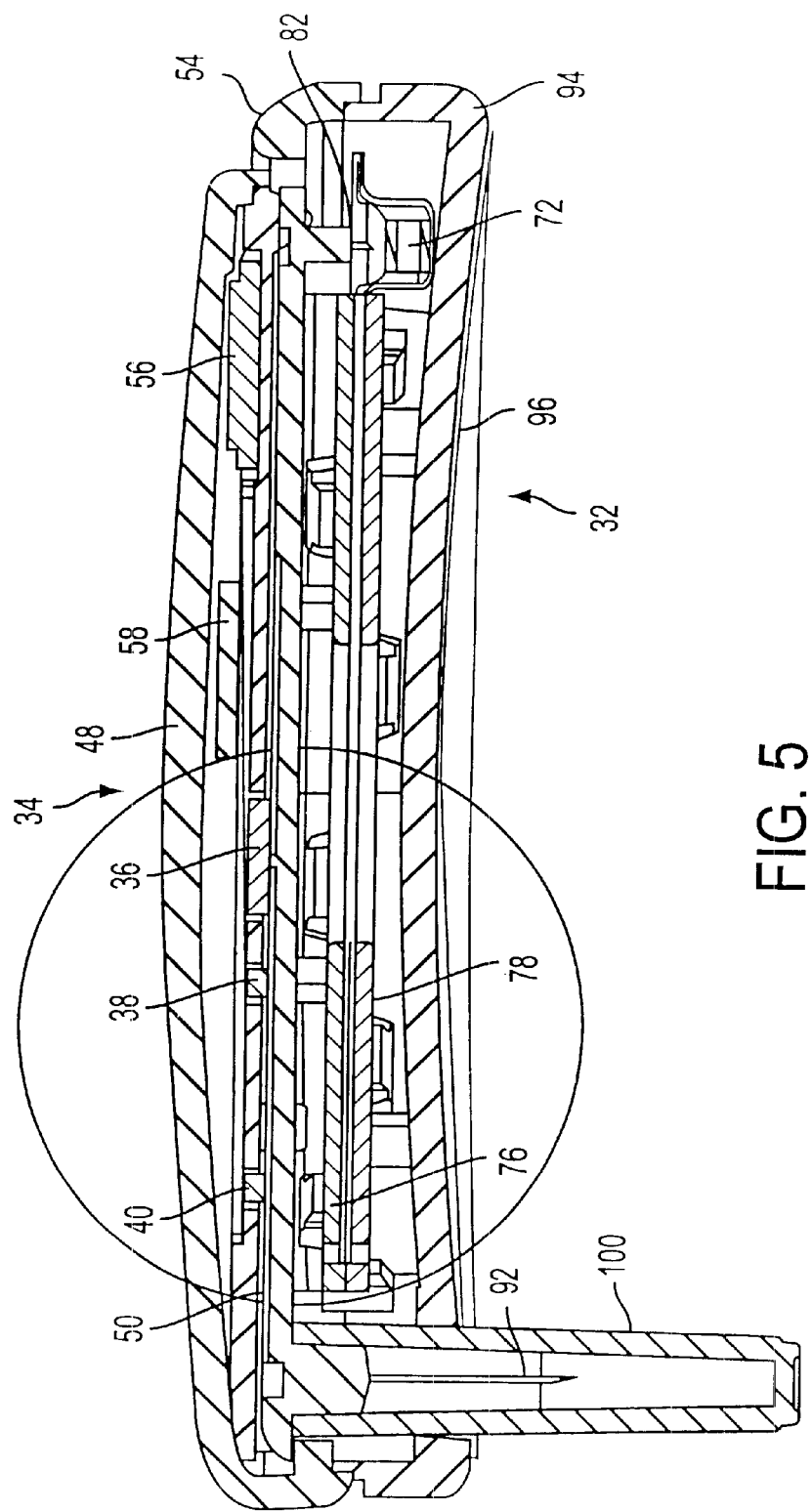
FIG. 5 is an enlarged cross-sectional view of the assembled drug infusion device shown in FIG. 1, taken along the line 5—5 in FIG. 1.

FIGS. 5, 6 and 7 are cross-sectional views of the assembled drug delivery device 30. FIG. 5 is an overall cross-sectional view taken along the line 5–5 in FIG. 1, while FIGS. 6 and 7 are magnified cross-sectional views illustrating the manner in which the flow of liquid medication from the pressurized reservoir is controlled by the piezoelectric element 36. In particular, FIG. 6 illustrates the fluid flow path with the piezoelectric element 36 in its de-energized condition, while FIG. 7 illustrates the fluid flow path with the piezoelectric element 36 energized to allow the flow of liquid medication to occur. Referring first to FIG. 6, the liquid medication enters the flow channel 55 at point 102 and exits at point 104. There is a discontinuity or dam 106 just under the center of the piezoelectric element 36. The flow channel 55 is capped by the thin membrane 50.

All of the components shown above the membrane 50 are part of the reusable portion 34 described previously. As illustrated there is a gap 108 between the bottom cover 46 of the reusable portion 34 and the membrane 50 everywhere except under the piezoelectric element 36, the thermal emitter 38 and the thermal detector 40. The gap 108 allows the piezoelectric element 36, thermal emitter 38 and thermal detector 40 to be forced into intimate contact with the top surface of the membrane 50. The presence of the dam 106 and the de-energized piezoelectric element 36 forced into contact above it prevents any flow of the liquid medication between the points 102 and 104 in FIG. 6. In FIG. 7, however, piezoelectric element 36 has been energized in response to a voltage output from the logic controller chip 58 of FIG. 3. In its energized condition, the piezoelectric element 36 flexes upward slightly as shown in FIG. 7. Since the fluid reservoir is pressurized by the Belleville spring disks 76 and 78 of FIG. 4, the liquid medication in the flow channel 55 on the right side of the dam 106 in FIG. 7 is also under pressure. As a result, when the piezoelectric element 36 flexes upwardly as shown in FIG. 7, the membrane 50 is forced upwardly by the fluid pressure and separates from the dam 106. This produces a liquid flow path from the entry point 102, over the dam 106, to the exit point 104. From the exit point 104, the liquid medication is conducted into the delivery cannula 92 and into the skin of the user. As can be appreciated from FIGS. 6 and 7, the upward and downward flexing of the piezoelectric element 36, in combination with the fixed dam 106, provides an on-off valve for the pressurized flow of liquid medication from the reservoir.

To provide precise control over the flow rate over the liquid medication through the channel 55, closed-loop control of the energization and the de-energization of the piezoelectric element 36 is desired. This requires that the actual flow rate of the liquid medication through the channel 55 be sensed while the valve formed by the piezoelectric element 36 and dam 106 is open (as shown in FIG. 7). This is achieved by means of the flow sensor formed by the thermal emitter 38 and thermal detector 40. When the piezoelectric element 36 is energized to open the valve, as shown in FIG. 7, the flow of liquid medication starts and almost immediately reaches its maximum rate. At this point, the thermal emitter 38 is momentarily energized with a pulse of current by the logic controller chip 58 of FIG. 3, and thus produces a small amount of heat which passes through the membrane 50 and into the liquid medication flowing in the channel 55. Once the pulse of heat is produced by the thermal emitter 38, the thermal detector 40 (under the control of the logic controller chip 58) begins to look for an abrupt but small rise in the temperature of the membrane 50 adjacent to the flowing liquid. The time lag between the pulse of heat from the thermal emitter 38 and its detection by the thermal detector 40 is measured by the logic controller chip 58 and is representative of the flow rate of the liquid medication in the channel 55. An internal lookup table in the logic controller chip 58 correlates the measured time delay with the flow rate of the liquid medication in the channel 55. The measured flow rate is then compared with the predetermined target value and the difference (if any) is used to adjust the duty cycle of the piezoelectric element 36. In this manner, the thermal emitter 38 and thermal detector 40 can not only maintain a desired flow rate in the channel 86, but can also provide real-time calibration for the device 30 in order to adjust for manufacturing tolerances and changing environmental conditions. The flow control algorithm used by the logic controller chip 58 uses the calibrated maximum flow rate value to energize and de-energize the piezoelectric element 36 in a pulsatile manner in accordance with the calculated duty cycle to obtain a predetermined flow rate that may have any desired value between zero and the maximum flow rate dictated by the reservoir pressure and the flow resistance of the channel 55. The predetermined flow rate may be a fixed flow rate that is programmed into the logic controller chip 58 during manufacture, a user-selected variable flow rate that is entered by means of an external input, or a programmed flow rate that varies automatically over the course of a day. Since the duty cycle of the piezoelectric element 36 can be varied as desired, an infinite gradation of flow rates is possible.

Figure 8:
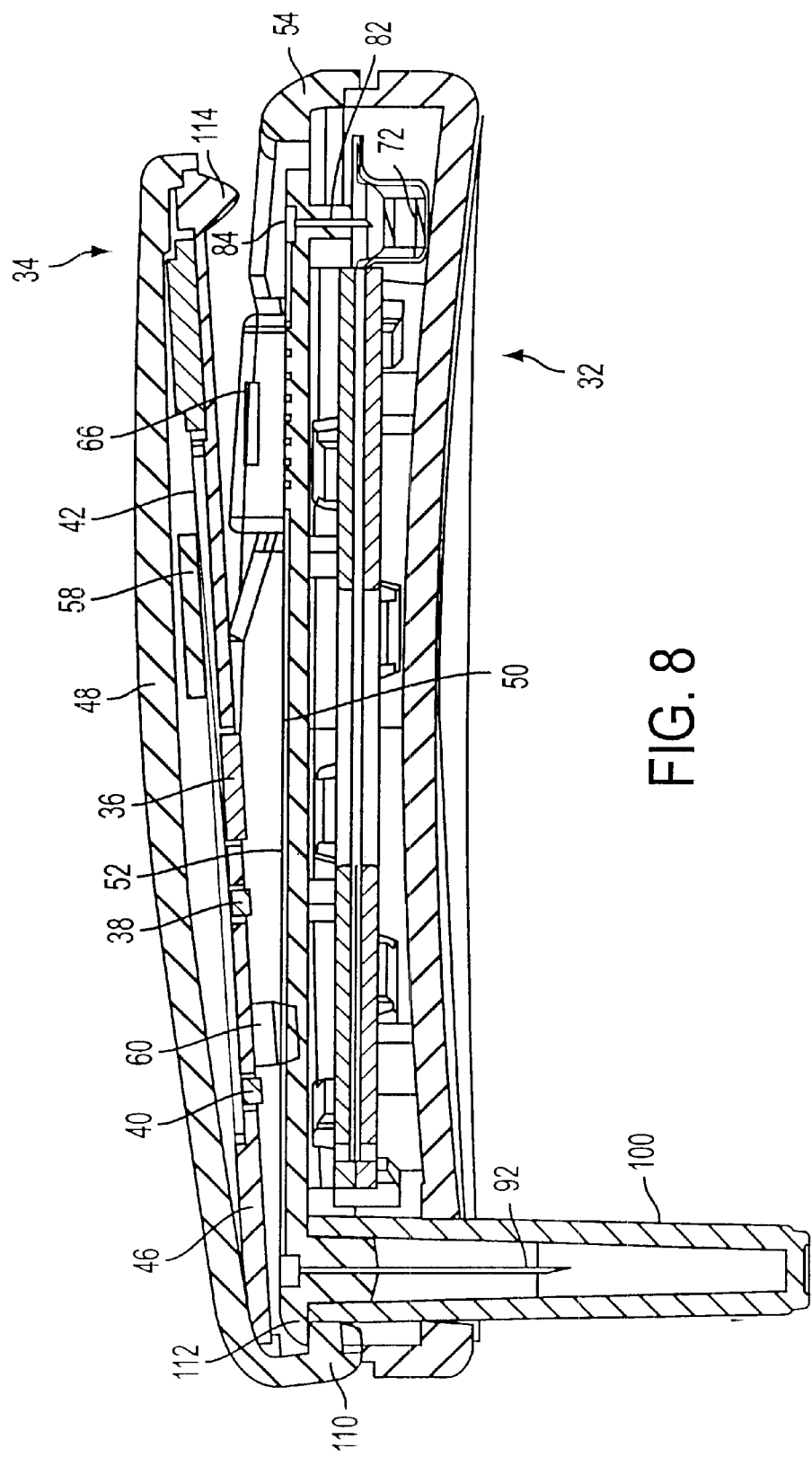
FIGS. 8 and 9 are cross-sectional views similar to that of FIG. 5, illustrating the operation of a fail-safe system which prevents the flow of liquid through the disposable portion of the drug infusion device when the reusable portion is not in place.
Figure 9:
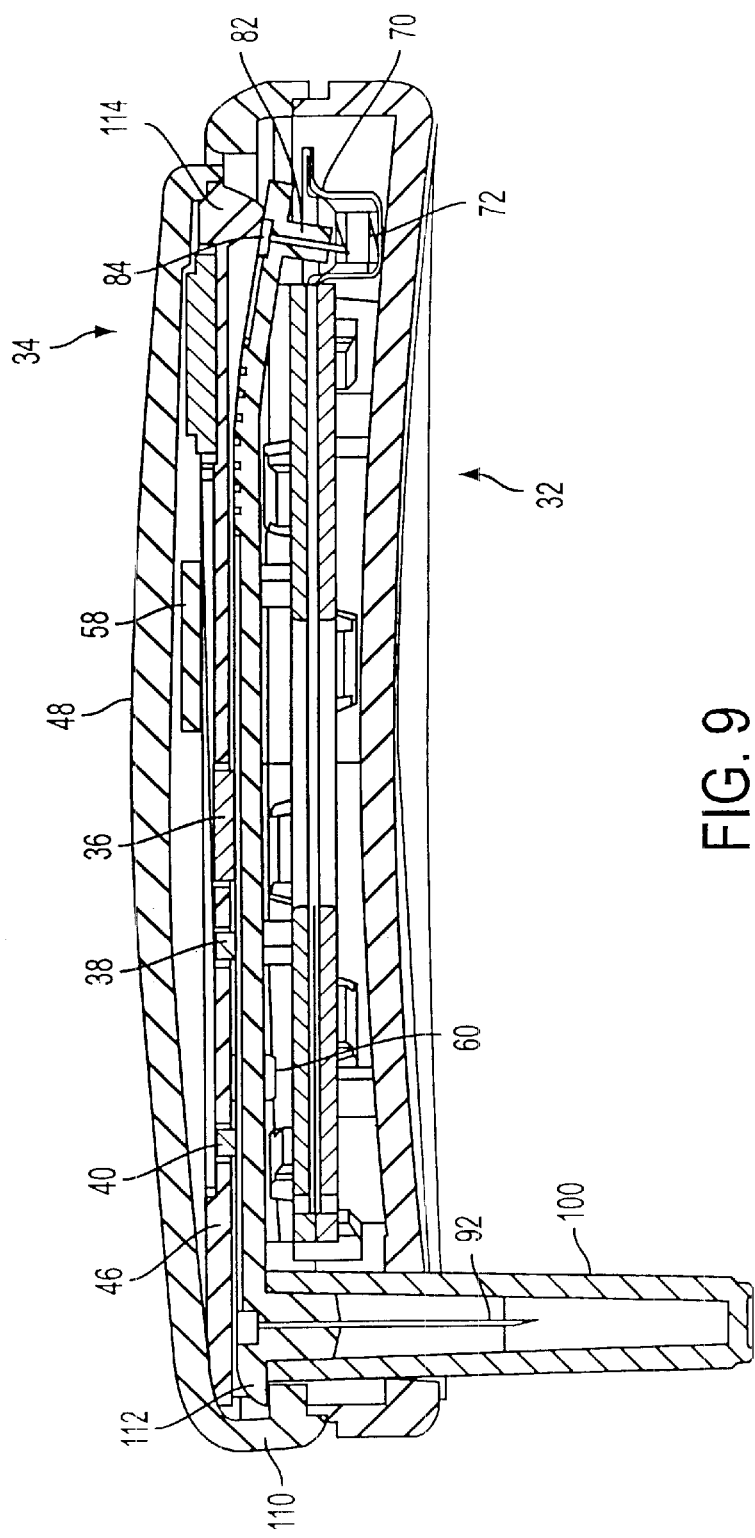

FIGS. 8 and 9 illustrate the functioning of a fail-safe system which prevents the flow of liquid medication through the channel 55 when the reusable portion 34 is not in place on the disposable portion 32 of the device 30. In FIG. 8, the reusable portion 34 is shown in the position it occupies just prior to being snapped down into place on the disposable portion 32. A tab 110 secures the left-hand end of the reusable portion 34 under a ledge 112 formed on the top cover 54 of the disposable portion 32. As the reusable portion 34 is rotated down into place, the locating tabs 60 on the bottom of the bottom cover 46 of the reusable portion 34 slip into the holes 62 in the top cover 54 of the disposable portion 32. This serves to align the piezoelectric element 36, thermal emitter 38 and thermal detector 40 with the flow path area 52. Just after the piezoelectric element 36, thermal emitter 38 and thermal detector 40 come into intimate forced contact with the membrane 50, a protuberance 114 contacts the top cover 54 near the channel inlet 84. A cut-out section 116 of the top cover 54 (visible in FIG. 4) is defined around the channel inlet 84, allowing this section of the flow path area 52 to deflect downwardly to provide a cantilever spring effect. Once the protuberance 114 makes contact with the cantilevered section of the flow path area 52, further downward movement of the reusable portion 34 is resisted by a slight spring force resulting from the downward deflection of the cantilevered section of the flow path area 52. This spring pressure serves the function of providing tactile feedback to the user of impending closure of the snap tabs 66 (FIG. 2), and also helps to push the reusable portion 34 upwardly and to separate it from the top cover 54 of the disposable portion 32 when the user desires to separate the disposable and reusable portions 32 and 34. The final actions which take place upon pushing the reusable controller into place arc the engagement of the tabs 64 (visible in FIGS. 2 and 3) on the sides of the top cover 48 of the reusable portion 34 with the corresponding tabs 66 formed on the top cover 54 of the disposable portion 32, thereby securing the reusable portion 34 in place on the disposable portion 32, and the simultaneous deflection of the cantilevered section of the flow path area 52 in a downward direction. This latter deflection causes the start cannula 82 to puncture the top membrane 68 of the liquid reservoir and the self-sealing septum 72, as shown in FIG. 9. Only when the start cannula 82 punctures the membrane 68 and septum 72 can the liquid medication enter the flow channel 55. Since the piezoelectric element 36 is already firmly in place against the membrane 50 at this point, thus blocking the channel 55 at the location of the dam 106, the liquid medication cannot reach the delivery cannula 92. Thus, the flow of liquid medication is under control at all times.

To facilitate the user s removal of the reusable portion 34 from the disposable portion 32, the snap tabs 66 are carried by removable release buttons 118 as shown in FIGS. 2 and 4. By pressing the release buttons 118, the tabs 66 can be disengaged from the corresponding tabs 64 on the sides of the reusable portion 34, thereby allowing the reusable portion 34 to be pivoted upward and removed from the disposable portion 32. When this occurs, the cantilevered section of the flow path area 52 springs upward to the position shown in FIG. 8, thereby assisting in the removal of the removable portion 38. At the same time, the upward movement of the cantilevered portion of the flow path area 52 causes the start cannula 82 to withdraw from the septum 72, causing the flow of liquid medication from the reservoir to cease. This occurs just before the piezoelectric element 36, thermal emitter 38 and thermal detector 40 lose control effectiveness. Thus, by the time these components become ineffective, further flow of the liquid medication through the channel 55 is no longer possible.

Figure 10:
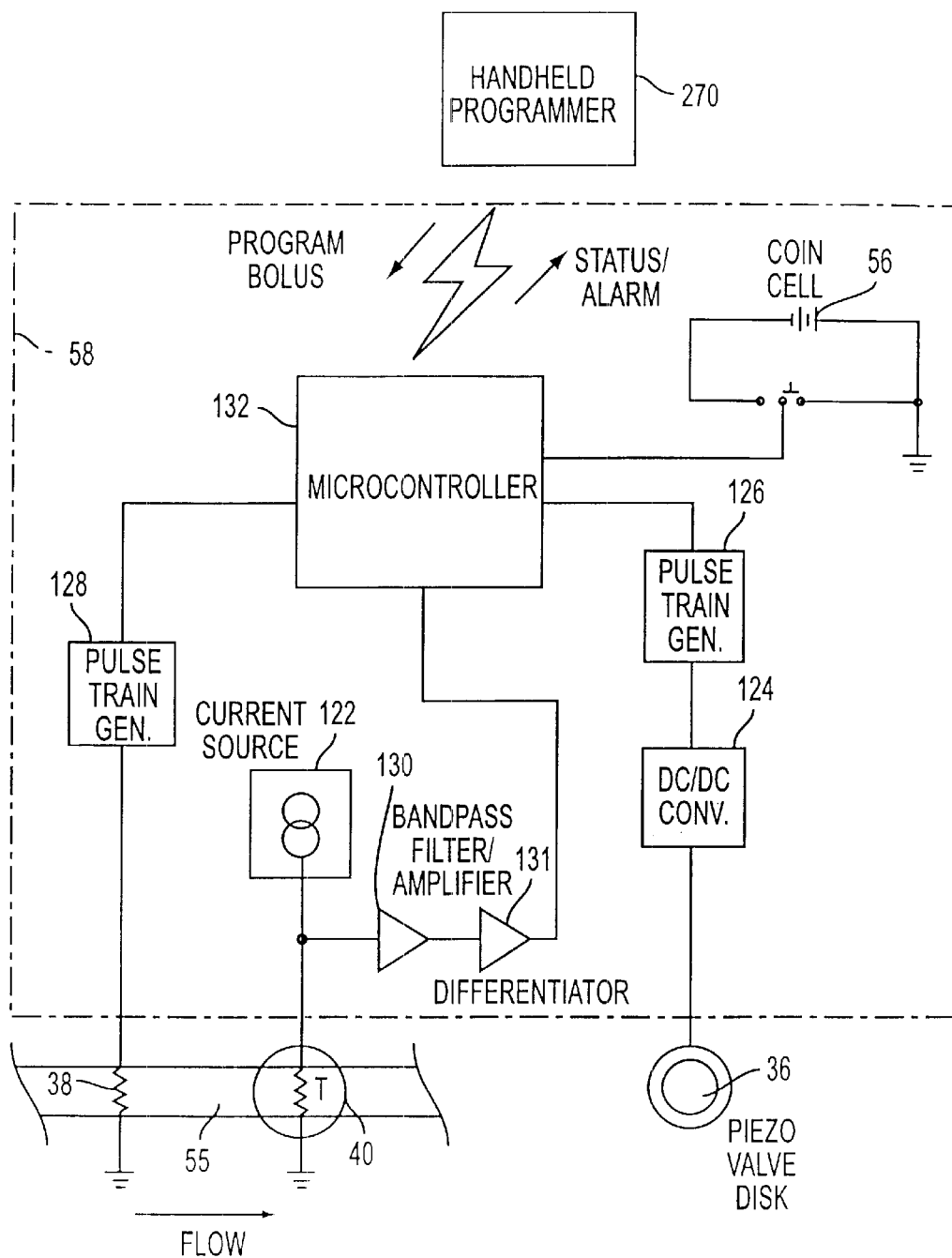
FIG. 10 is a block diagram illustrating the principal electrical components housed in the reusable portion of the drug infusion device of FIGS. 1–9.

FIG. 10 is a block diagram which illustrates the principal electrical components of the reusable portion 34 of the drug infusion device 30. Included in FIG. 10 are the piezoelectric element 36 and logic controller 58 of FIG. 3, a portion of the flow channel 55 of FIG. 4, and a wireless handheld programmer 270 for the logic controller 58. Associated with the flow channel 55 are the thermal emitter 38 and thermal detector 40, the thermal detector 40 being located downstream of the thermal emitter 38 relative to the direction of fluid flow. The flow channel 55 and its associated components are shown schematically in FIG. 10, but it will be understood that the thermal emitter 38 and thermal detector 40 are not, in the preferred embodiment of the invention, physically present within the channel 55 but instead are separated from the channel 55 by the membrane 50 of FIG. 4. The thermal emitter 38, which is preferably a common surface mount resistor, is controllably driven by a pulse train generation circuit 128 which is in turn controlled by a microcontroller 132. The pulse train generation circuit 128 is configured to produce one or as many as four square wave voltage pulses of 1–2 seconds duration at a 50% duty cycle. It requires only a single output trigger from the microcontroller 132 to begin. The thermal detector 40, which is preferably a small thermistor element, is controllably driven by a current source 122 such that it produces a voltage that is directly proportional to its resistance, and inversely proportional to its temperature. This voltage is coupled to the input of a bandpass filter/amplifier 130. The output of the bandpass filter/amplifier 130 is coupled to the input of a differentiator amplifier 131, whose output is coupled directly to an input of the microcontroller 132. Any changes in the temperature of the liquid flowing in the flow channel 55 effect a change in the resistance of the thermistor 40 and hence a change in the voltage at the input of the bandpass filter/amplifier 130. The bandpass filter/amplifier 130 acts to filter out any frequencies above that produced by the pulse train generator 128, and to amplify the resulting signal for the next stage. The differentiator 131 will produce a quick spike signal at the input of the microcontroller 132 when its input receives a voltage change at a frequency that would pass through the bandpass filter/amplifier 130. The overall effect of this circuit is to apply a sharp rising edge signal to the microcontroller 132 whenever the thermal detector 40 senses the flow channel heat signal from the thermal emitter 38. Based on the measured time delay between energization of the thermal emitter 38 and detection of a signal from the thermal detector 40, the microcontroller 132 determines the instantaneous volumetric flow rate of the liquid medication in the flow channel 55. The measured flow rate is compared with the desired value and used by the microcontroller 132 to energize the piezoelectric element 36 with a variable duty cycle by means of a pulse train generator 126 and a DC-to-DC converter 124. The DC-to-DC converter increases the voltage amplitude at the output of the pulse train generator 126 to a level that is adequate to drive the piezoelectric element 36.

Determination of the flow rate of the liquid medication in the flow channel 55 of FIG. 10 is carried out with the use of a stored lookup table. A measured time delay value representing the interval between energization of the thermal emitter 38 and detection of an elevated fluid temperature at the thermal detector 40 is converted to a memory address and applied as an input to a memory device (not shown) within the control microcontroller 132 of FIG. 10. The output of the memory device is the corresponding liquid flow rate value, which is compared with the known target value and used to increase or decrease the duty cycle of the piezoelectric element 36 as required to maintain the user-defined flow rate. In this way, the desired closed-loop control is achieved. The measured flow rate value may also be used to provide an alarm or status output to the user, as will be discussed below in connection with the wireless programmer 270. Typically, the measured time delay value will not precisely match any of the reference values which are used to access the flow rates stored in the memory device. In these instances, a linear interpolation procedure can be used.

In order to compile the look-up table in the first instance, empirical measurements may be made in a laboratory setting using a channel geometry identical to that used in the drug infusion device 30. A known flow rate of insulin is established in the channel and a corresponding time delay value is obtained by applying a pulse train to the thermal emitter 38 and measuring the time elapsed until the resulting rise in liquid temperature in the channel is detected by the thermal detector 40. This procedure is repeated for a number of flow rates (preferably about 10) to produce a corresponding number of time delay values. The flow rates corresponding to these values arc then stored in the memory device of the microcontroller 132 at addresses that can be correlated to the measured time delay values.

As an alternative to the empirical method, a mathematical formula may be used to relate flow rates to time delay values. The following parameters are employed:

Time Lag=The actual measured amount of time between initiation of a pulse train at the thermal emitter 38 and the receipt of the differentiator 131 output at the microcontroller 132. Time Lag is equal to the sum of Time of Flight, Conduction Lag and Convection Lag.

Conduction Lag=The amount of time required for the thermal emitter 38 to heat itself, the upstream portion of the membrane 50, the downstream portion of the membrane 50, and the thermal sensor 40.

Convection Lag=The amount of time required for the heat produced by the thermal emitter 38 to be sensed by the thermal detector 40 based on convection into the liquid in the flow channel 55 from the upstream portion of the membrane 50.

Time of Flight=A calculated parameter which is equivalent to the amount of time required for the liquid medication to physically flow from the thermal emitter 38 to the thermal detector 40 at the current flow rate being measured.

It is assumed that the Conduction Lag and Convection Lag parameters are both constants for the drug infusion device 30 when manufactured in large quantity at controlled tolerances. These constants can be determined empirically from a large sample of finished devices 30, and can be used to create the lookup table for Flow Rate versus Time Lag. The lookup table is created by applying the following mathematical formula to the data collected:

Flow Rate=Volume of flowpath between stations[Time Lag−(Conduction Lag+Convection Lag)]

As a further alternative, the mathematical formula set forth above may be used by the microcontroller 132 of FIG. 10 to calculate flow rate values in real time. This would avoid the need to compile and store a lookup table, but it would also place a greater computational burden on the microcontroller 132 during normal operation of the drug infusion device 30.

Figures 11A, 11B:
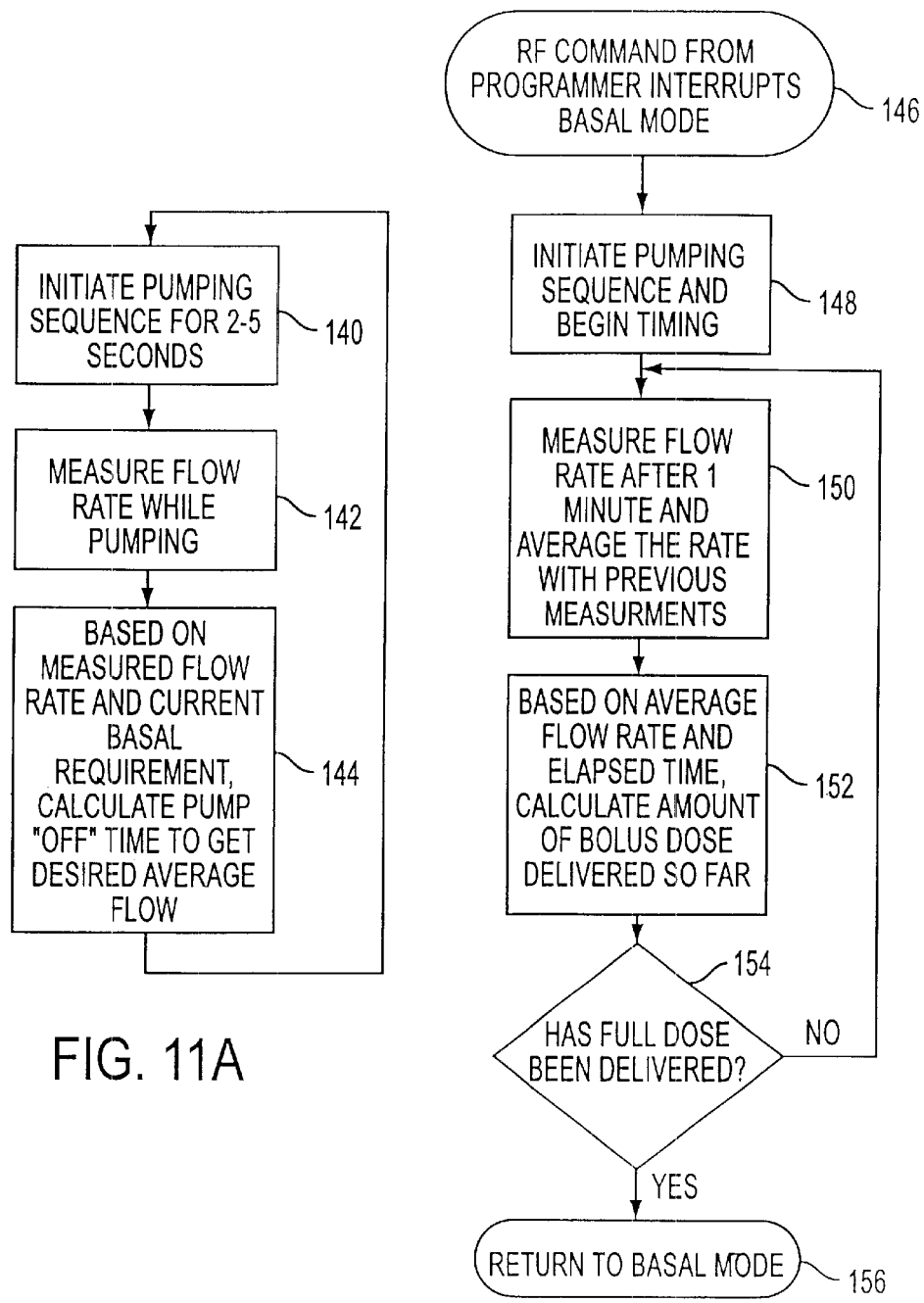
FIGS. 11A–11E are flow charts illustrating the sequence of operations carried out by the microcontroller in the block diagram of FIG. 10.
Figure 11C:
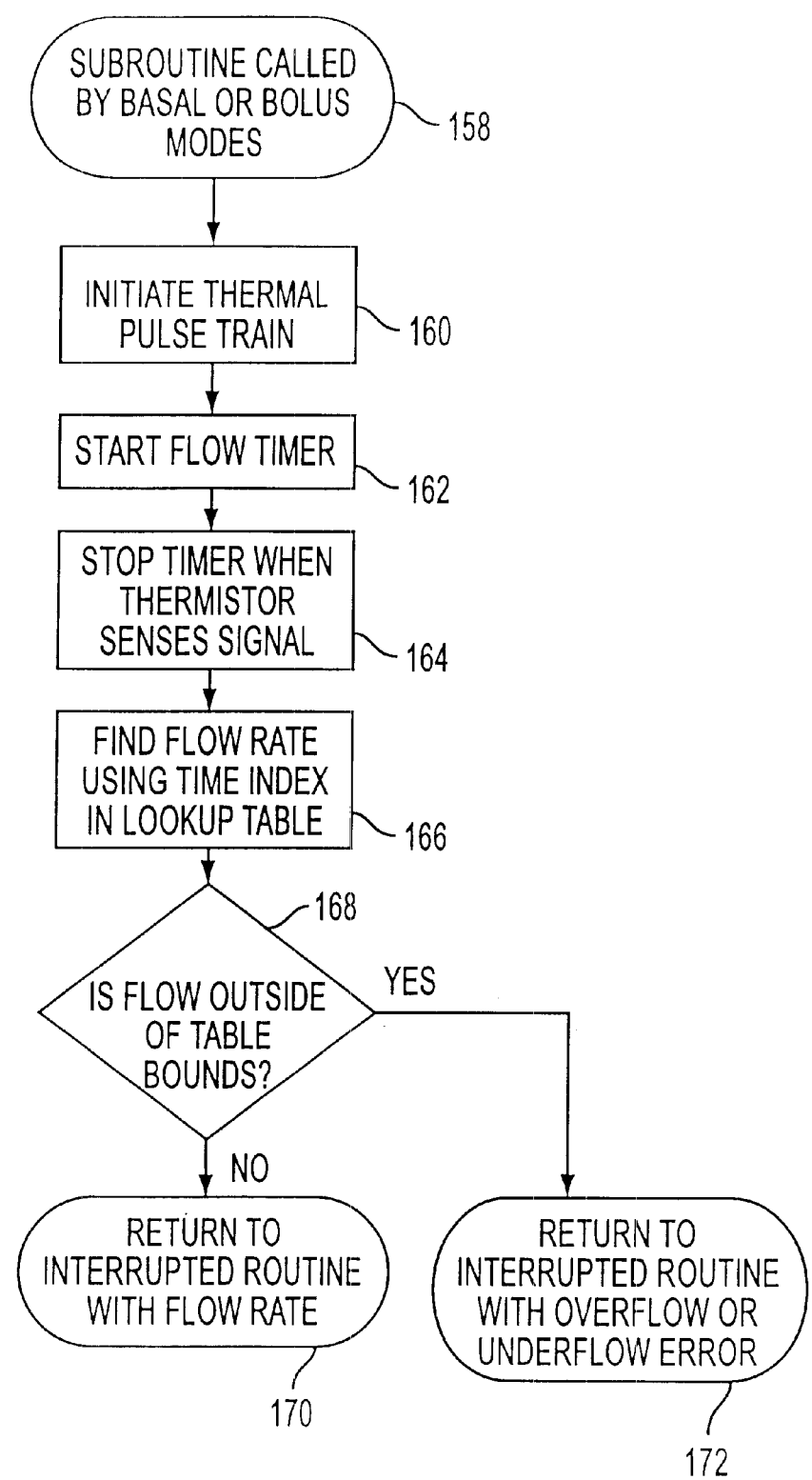

FIGS. 11A–11E are flow charts which describe the operation of the microcontroller 132 of FIG. 10. FIG. 11A describes the operation of the microcontroller 132 during the basal delivery (default) mode of the drug infusion device 30, while FIG. 11B describes the operation of the microcontroller 132 when a bolus delivery is requested by the user. FIG. 11C is a microcontroller subroutine which is used for flow rate sensing, while FIG. 11D describes a microcontroller subroutine which is called when the user wishes to load a new daily program into the drug infusion device 30. Finally, FIG. 11E describes a subroutine which is called by the microcontroller when status information is to be exchanged between the logic controller 58 and handheld wireless programmer 270 of FIG. 10.

Referring first to FIG. 11A, the microcontroller 132 begins the basal delivery mode in block 140 by initiating the flow of liquid medication in the flow channel 55 for a period of between 2 and 5 seconds. In block 142, the subroutine of FIG. 11C (to be described shortly) is called to measure the resulting flow rate. Based on the measured flow rate and the user's current basal requirement, the microcontroller 132 calculates in block 144 the duty cycle of the piezoelectric element 36 that is required to achieve the desired average flow rate. This duty cycle is then employed as a the nominal value during the next pass through the flow chart of FIG. 11A, and is adjusted as necessary to maintain the average flow rate at the target value. This process continues indefinitely during normal operation of the drug infusion device 30.

FIG. 11B illustrates the operation of the microcontroller 132 during the bolus delivery mode. This mode may be triggered by the user prior to mealtimes or whenever a bolus delivery of insulin is required. In block 146, a bolus delivery command from the wireless programmer 270 is received by the logic controller 158 and causes the microcontroller 132 to interrupt basal mode delivery. In block 148, the microcontroller 132 modifies the duty cycle of the piezoelectric element 36 to 100% "on" and 0% "off" so that the flow channel 55 is continually open. In block 150, the resulting flow rate in the flow channel 55 is measured after one minute and is averaged with previous measurements. In block 152, the microcontroller 132 calculates the total volume of bolus dose which has been delivered so far based on the average flow rate and the elapsed time. In block 154, a determination is made as to whether the full bolus dose has been delivered. If it has not, the microcontroller returns to block 150 and repeats the steps described in blocks 150–154. Once it is determined in block 154 that the full bolus dose requested by the user has been delivered, the microcontroller proceeds to block 156 and returns to the basal delivery mode of FIG. 11A.

The flow rate sensing subroutine carried out by the microcontroller 132 is illustrated in FIG. 11C. As indicated in block 158, this subroutine may be called by the microcontroller 132 either during the basal delivery mode of FIG. 11A or during the bolus delivery mode of FIG. 11B. In block 160, the microcontroller 132 initiates a pulse train by the pulse train generator 128 of FIG. 10. This causes heat to be generated in the flow channel 55 by the thermal emitter 38. In block 162, a flow timer is started in the microcontroller 132. In block 164, an input from the differentiator 131 of FIG. 10 causes the microcontroller 132 to stop the flow timer. In block 166, the value of the flow timer is read and is used to obtain a corresponding flow rate value from the lookup table in the memory of the microcontroller 132. In block 168, the microcontroller 132 determines whether the flow rate is within the range of values contained in the lookup table. If it is, the microcontroller 132 simply returns in block 170 to the interrupted routine (i.e., to the basal delivery mode of FIG. 11A or the bolus delivery mode of FIG. 11B) along with flow rate value required by that routine. However, if the flow rate is outside the range of values contained in the lookup table, the microcontroller returns in block 172 to the interrupted routine with an indication of an overflow or underflow error. The error indication causes the microcontroller 132 to generate an alarm to the user via the wireless programmer 270 of FIG. 10.

Figure 11D:
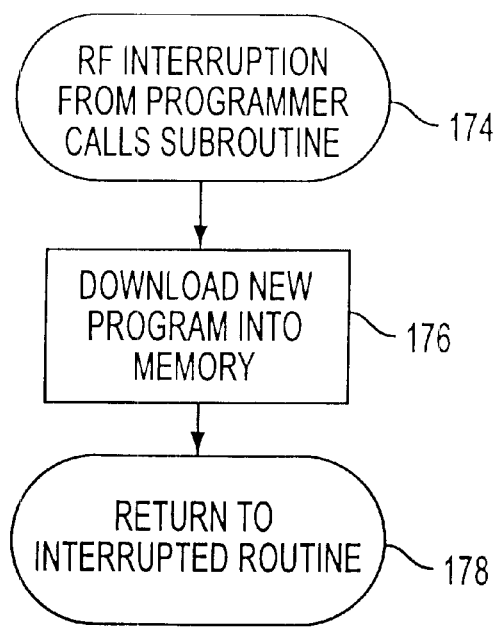

FIG. 11D describes a subroutine which is called by the microcontroller 132 of FIG. 10 when the user desires to enter a new liquid medication delivery program into the drug infusion device 30, or to update a previously-entered program. In block 174, the receipt of an RF signal from the wireless programmer 270 of FIG. 10 causes the microcontroller 132 to call the subroutine. In block 176, the new delivery program is received from the wireless programmer 270 and entered into the memory of the microcontroller 132. In block 178, the microcontroller 132 returns to the routine (typically the basal mode routine of FIG. 11A or the bolus mode routine of FIG. 11B) which was interrupted by the subroutine of FIG. 11D.

Figure 11E:
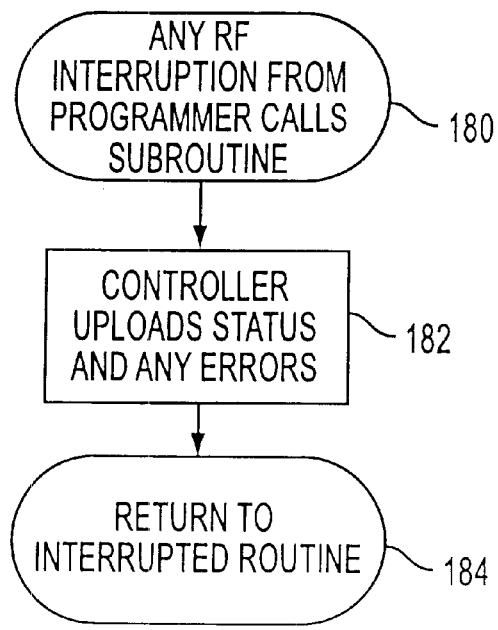

FIG. 11E illustrates a subroutine which is called by the microcontroller 132 to exchange status information with the wireless programmer 270 of FIG. 10. In block 180, the receipt of an RF signal from the wireless programmer 270 causes the microcontroller 132 to call the subroutine. This signal may result from a user input or may be produced periodically and automatically by the wireless programmer 270 without any action by the user. In block 182, the microcontroller 132 causes the logic controller 58 to upload status information and error indications (alarms) to the wireless programmer 270. Once this process is complete, the microcontroller 132 proceeds to block 184 and returns to the routine that was interrupted when the subroutine of FIG. 11E was called.

Several modifications are possible in the embodiment of FIGS. 1–10 and 11A–11E. For example, the piezoelectric element 36 may be relocated from the reusable portion 34 of the drug infusion device 30 to the disposable portion 32 (e.g., by bonding the element 36 to the top surface of the membrane 50). Also, the thermal emitter 38 and thermal sensor 40 may be formed as films or layers (e.g., by silk screening or the like) directly on the membrane 50. For example, by forming the thermal emitter 38 and thermal sensor 40 on the underside of the membrane 50, they may be placed in direct contact with the liquid medication in the flow channel 55 and may thus operate more efficiently. As a further modification, additional thermal detectors 40, either upstream or downstream of the thermal emitter 38, may be added to improve the quality of the signal by anticipating changes in ambient temperature conditions.

FIGS. 12–17 illustrate the disposable portion of a drug infusion device 200 constructed in accordance with a second embodiment of the present invention. This embodiment differs from the first embodiment of FIGS. 1–10 and 11A–11E in the manner by which motive force is applied to the liquid medication for its delivery. In the first embodiment, a reservoir with externally applied spring force is utilized to pressurize the liquid medication. The pressurized liquid then passes through a piezoelectric valve which is modulated under electronic control to produce a controlled flow rate. In the embodiment of FIGS. 12–17, by contrast, a pressurized reservoir is not required. The motive force for the liquid medication is provided by a micropump which comprises two injection-molded plastic parts, two membranes, and a piezoelectric element driven by electronic control. As in the first embodiment, a reusable portion (not shown in FIGS. 12–17 but externally similar to the reusable portion 34 of FIG. 2) containing the required electronic components is provided as a separate unit which snaps into place on a disposable portion containing the liquid medication. This avoids the need for sealing the liquid flow path and eliminates the risk of leakage or contamination of the liquid medication. The only materials contacting the liquid medication are, as before, plastic parts or membranes. The embodiment of FIGS. 12–17 is also similar to the previous embodiment in that a thermal flow sensor is employed to allow for closed-loop control of the liquid flow rate through the delivery cannula. The electronic control system for the second embodiment of FIGS. 12–17 (and for the third embodiment of FIGS. 18 and 19, to be described hereinafter) is not described in detail herein, but will be understood to be similar to that of FIGS. 10 and 11A–11E.

Figure 12:
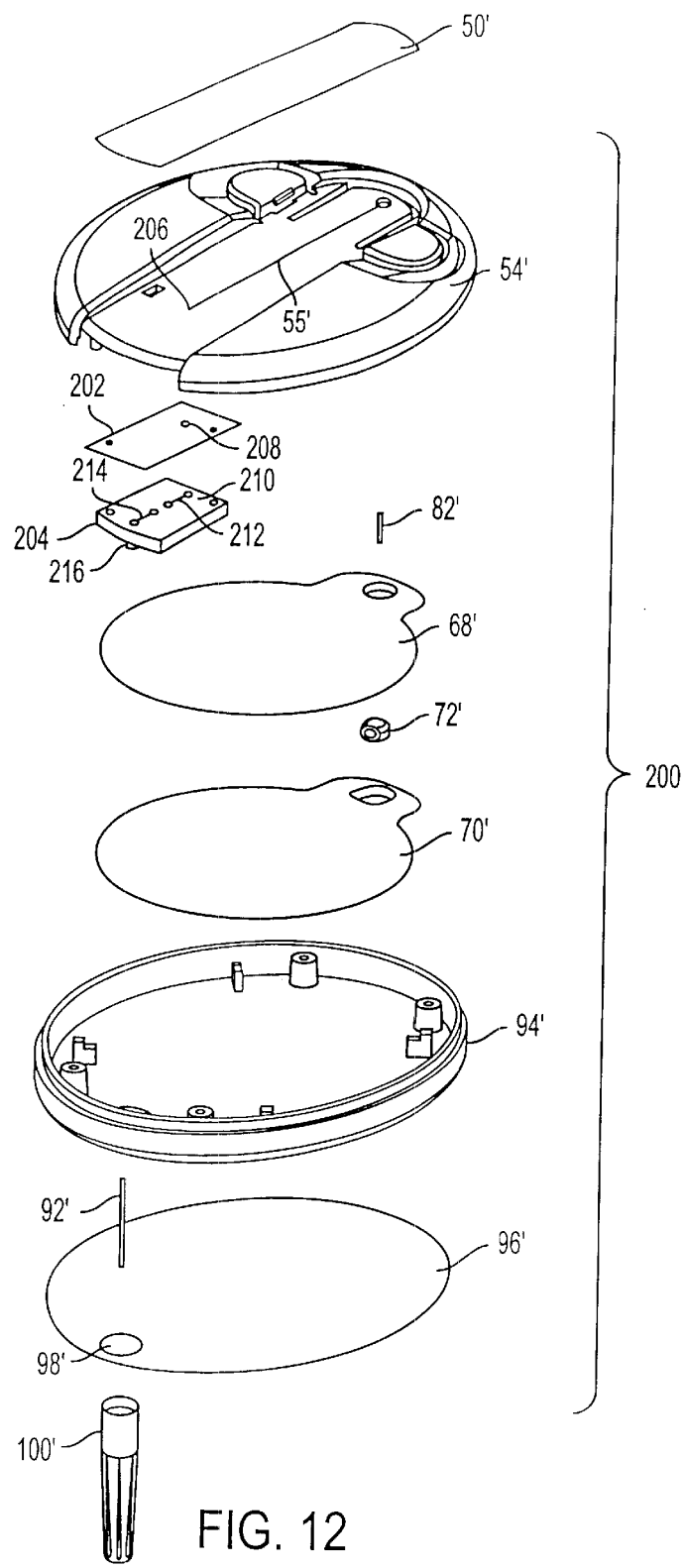
FIG. 12 is an exploded perspective view similar to that of FIG. 4, illustrating the disposable portion of a drug infusion device constructed in accordance with a second embodiment of the present invention.

FIG. 12 is an exploded view of the drug infusion device 200 in accordance with the second embodiment of the present invention. Parts of the device 200 which are similar or identical to those of the device 30 of the first embodiment are labeled with corresponding reference numerals (with primes added). Several features unique to the second embodiment may be observed in FIG. 12. First, unlike the device 30, the device 200 of FIG. 12 utilizes a reservoir assembly which consists only of the membranes 68' and 70' and does not include the Belleville spring disks 76 and 78. Since the reservoir is not pressurized, the Belleville spring disks 76 and 78 are not required. For the same reason, the serpentine area 86 of the flow channel 55 in the device 30 is not required in the flow channel 55' of the device 200. Finally, the device 200 differs from the last device 30 in that it includes a modified top cover 54' that cooperates with a valve membrane 202 and a lower valve body 204. These two components, in combination with the lower side of the top cover 54' acting as an upper valve body, form a micropump that is driven by a piezoelectric element (not shown in FIG. 12) located in the disposable portion of the device 200.

As in the previous embodiment, the liquid medication is contained in a reservoir formed by the membranes 68' and 70', which are sealed together with a septum 72' between them. A start cannula 82' is epoxy-bonded to a hub in the top cover 54', and pierces the septum 72' to start the flow of liquid medication to a flow channel 55' in the top surface of the top cover 54'. The flow channel 55' is sealed at the top by a membrane 50' and carries the liquid medication past the flow sensor of the reusable portion, as in the previous embodiment. At the end opposite to the start cannula 82', the flow channel 55' communicates with a hole 206 formed vertically through the top cover 54'. The hole 206 is aligned with a somewhat larger hole 208 formed in the valve membrane 202. The liquid medication passes through the aligned holes 206 and 208 and enters one end 210 of an inlet channel 212 that is formed in the top surface of the lower valve body 204. After passing through a pair of check valves (to be described shortly), the liquid medication flows through an outlet channel 214 in the lower valve body 204 and exits through a delivery cannula 92'. The delivery cannula 92' is carried by a cannula hub 216, which extends integrally from the bottom of the lower valve body 204. The inlet and outlet channels 212 and 214 are open at the top but are closed by the valve membrane 202 in the assembled condition of the device 200.

Figure 14:
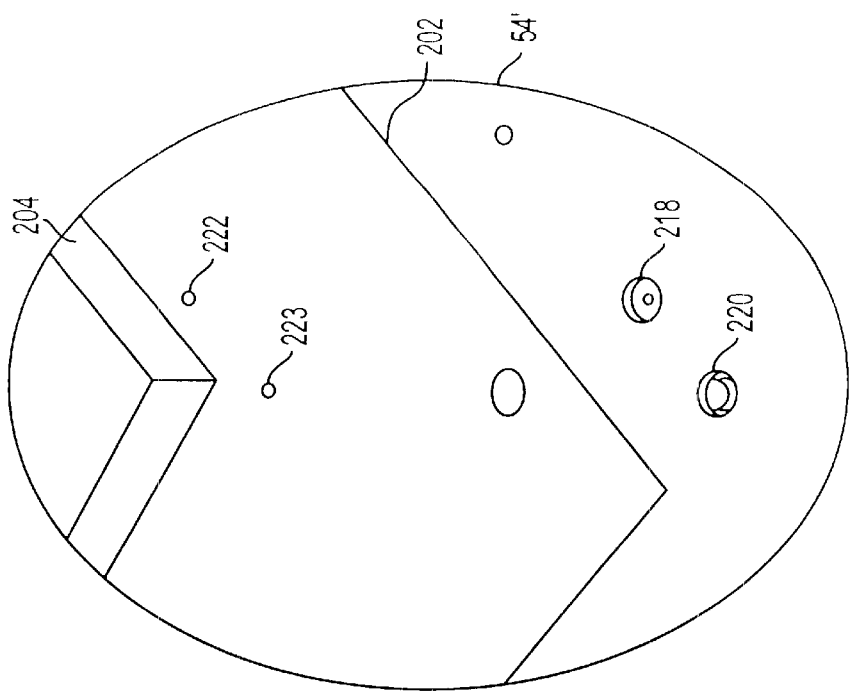
FIG. 14 is a magnified view of the circled area shown in FIG. 13.
Figure 13:
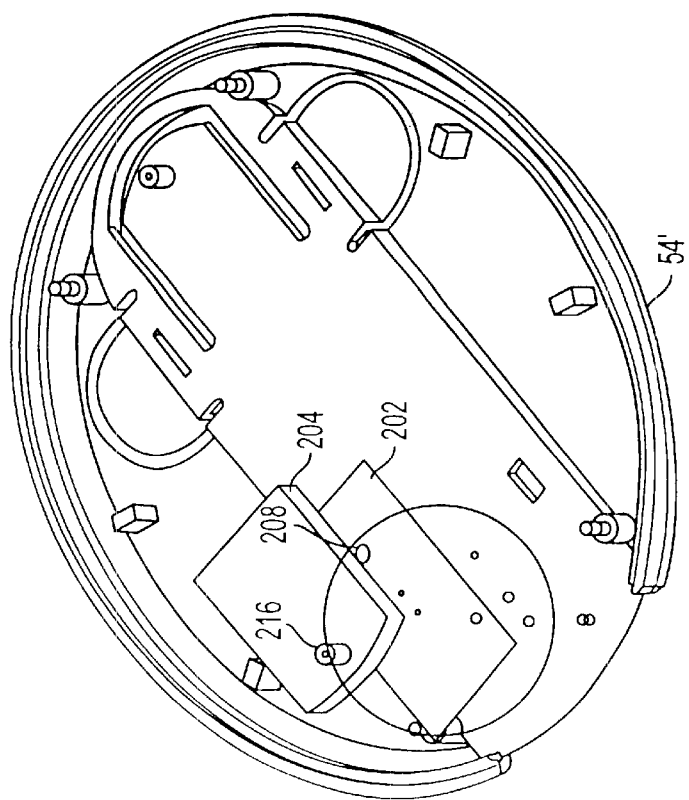
FIG. 13 is an enlarged, exploded perspective view in which certain of the components shown in FIG. 12 are viewed from the bottom.

FIG. 13 illustrates the top cover 54', valve membrane 202 and lower valve body 204 as they appear from a bottom view. Preferably, these three components are secured together by laser welding so that very accurate and leak-free seals are created. FIG. 14 is a magnified view of the circled area shown in FIG. 13, illustrating the upstream and downstream check valves 218 and 220 which are formed in the lower surface of the top cover 54'. Laser-drilled flow holes 222 and 223 are formed in the valve membrane 202 and are centered over the check valves 218 and 220, respectively.

Figure 15:
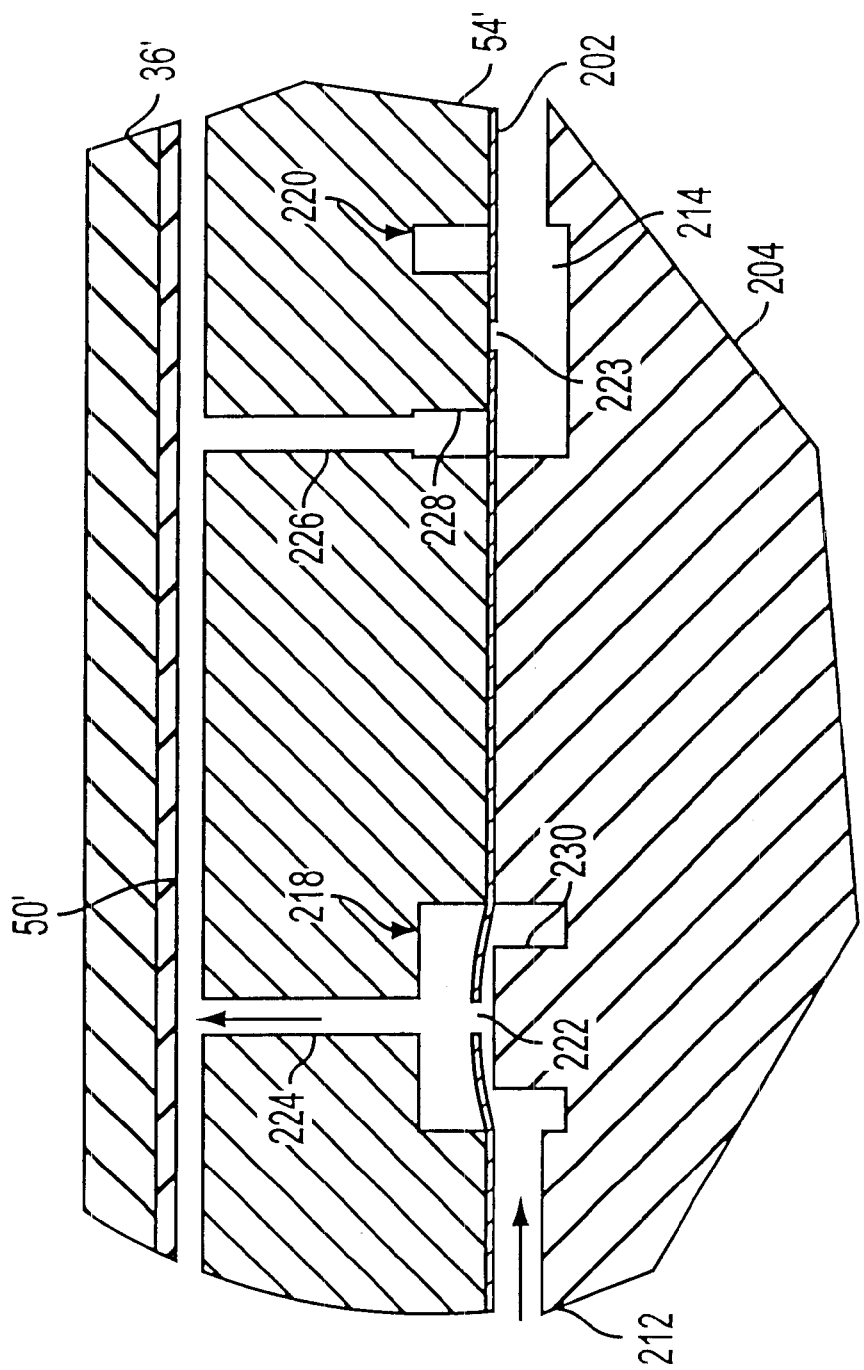
FIG. 15 is a magnified cross-sectional view of the piezoelectric pump used in the disposable portion of the embodiment shown in FIGS. 12–14, as it appears during the fluid intake stroke.
Figure 16:
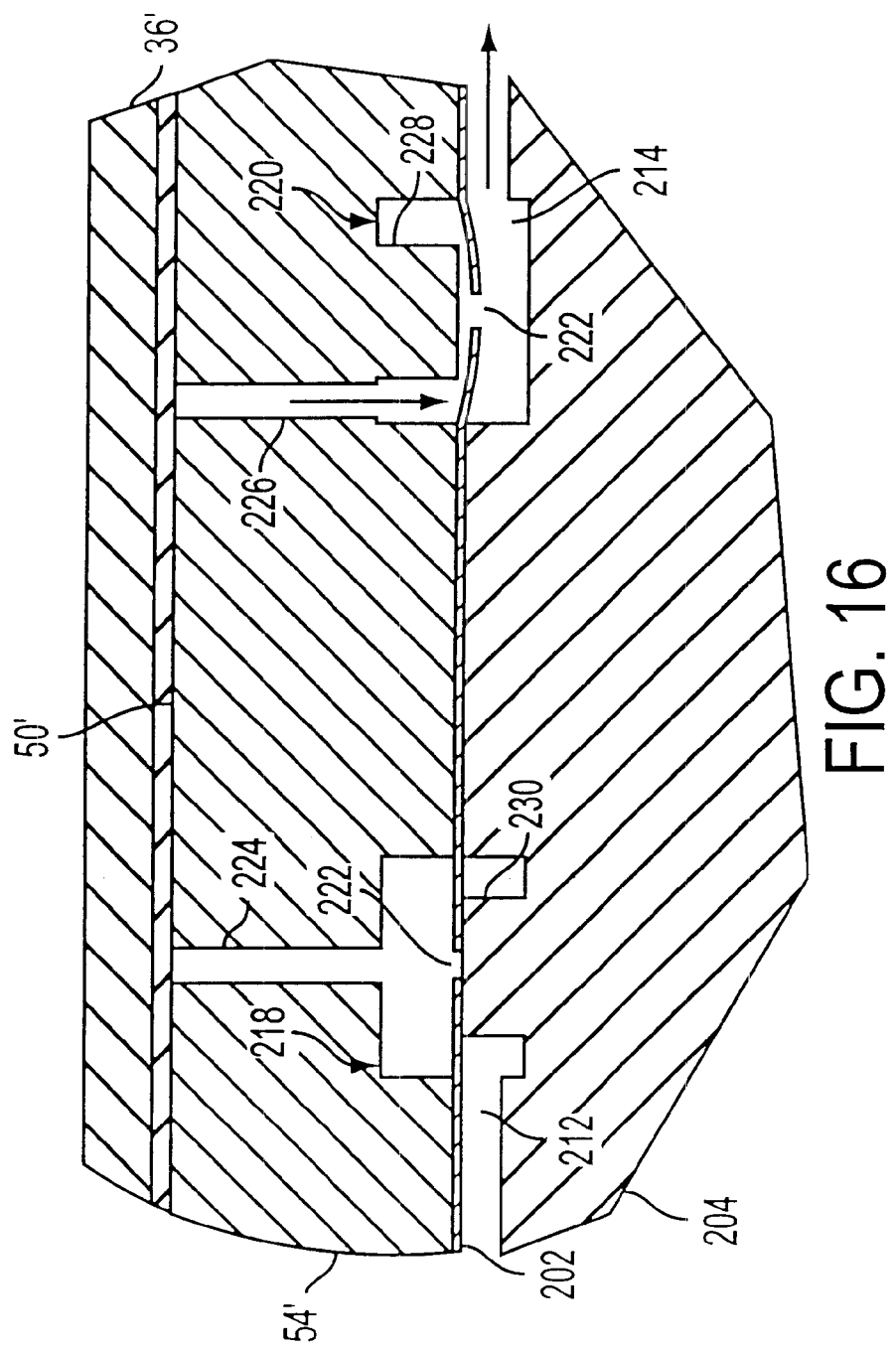
FIG. 16 is a magnified cross-sectional view similar to that of FIG. 15, showing the fluid exhaust stroke of the piezoelectric pump.

The operation of the check valves 218 and 220 during the pump intake and exhaust strokes is illustrated in FIGS. 15 and 16. To understand these views, it should be pointed out that the piezoelectric element 36' is, in this embodiment, preferably made a part of the disposable portion of the device 200 rather than a part of the reusable portion. With this modification, it becomes possible to adhesively bond the lower surface of the piezoelectric element 36' to the upper surface of the membrane 50', which in turn allows the piezoelectric element 36' to force the membrane 50' in either an upward or downward direction. This allows the check valves 218 and 220 to operate in the manner illustrated in FIGS. 15 and 16, as will be described below. Aligned metal contacts (not shown) may be provided in the disposable and reusable portions of the device 200 to provide electrical continuity between the piezoelectric element 36' and the drive circuitry in the reusable portion of the device 200. As an alternative to placing the piezoelectric element 36' in the disposable portion, it may be placed in the reusable portion (as in the embodiment illustrated in FIGS. 1–10 and 11A–11E) and adhered temporarily to the upper surface of the membrane 50' when the disposable and reusable portions are coupled together, as for example by means of a tacky layer or a film of viscous oil.

Against this background, the pump intake and exhaust strokes of FIGS. 15 and 16 may now be explained. During the intake stroke of FIG. 15, the piezoelectric element 36' is energized and bows upwardly, pulling up the membrane 50' on the top cover 54'. This creates a vacuum beneath the membrane 50', which is transmitted to the check valves 218 and 220 through laser-drilled holes 224 and 226, respectively, formed in the top cover 54'. At the downstream check valve 220, which is located nearest to the delivery cannula 92', the valve membrane 202 is pulled upward. This acts to seal off the flow hole 223 against the seat 228 of the downstream check valve 220. At the same time, the vacuum pulls the valve membrane 202 in an upward direction away from the seat 230 of the upstream check valve 218, thereby allowing the liquid medication to pass through the flow hole 222 of the check valve 218 from the inlet channel 212. The flow of liquid medication passes through the upstream check valve 218, through the laser-drilled hole 224, and into the cavity formed under the piezoelectric element 36' and membrane 50'. At this point, the intake stroke ends and the exhaust stroke of FIG. 16 begins. The drive voltage to the piezoelectric element 36' is terminated and the piezoelectric element 36' collapses to a flat state, thereby creating an elevated pressure in the liquid-filled cavity beneath the membrane 50'. This pressure is transmitted to the check valves 218 and 220 via the laser-drilled holes 224 and 226.

On the inlet side, this elevated pressure forces the valve membrane 202 against the valve seat 230 and prevents the liquid medication from flowing back into the reservoir. On the outlet side, the pressure causes the valve membrane 202 to separate from the valve seat 228 and thereby opens the flow path through the valve membrane 202 to the outlet channel 215, hub 216 and delivery cannula 92'. At this point, the exhaust stroke is complete and a new intake stroke may begin. During each intake and exhaust cycle, predetermined quantity of liquid medication is delivered to the user through the delivery cannula 92'.

Figure 17:
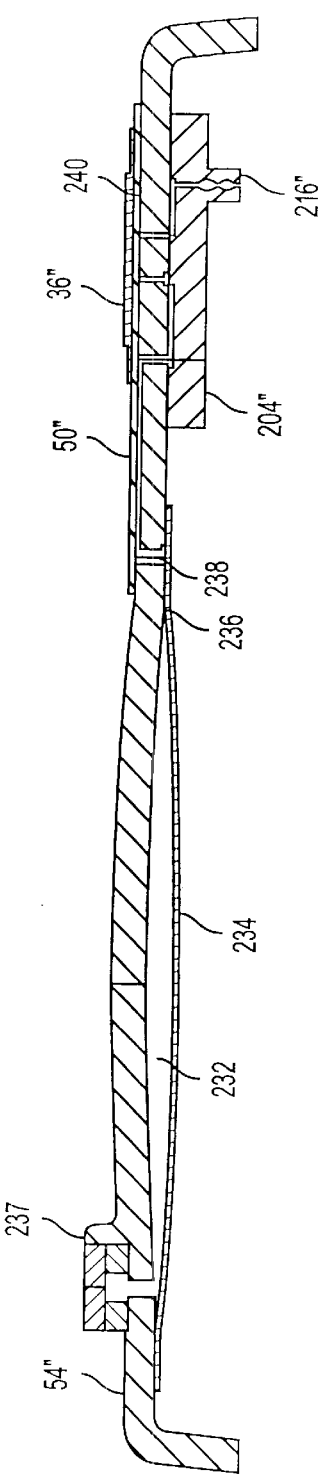
FIG. 17 is a cross-sectional view through the top cover of the disposable portion of a drug infusion device in a modification of the embodiment shown in FIGS. 12–16.

FIG. 17 is cross-sectional view through the top cover 54" of a modified version of the embodiment shown in FIGS. 12–16. In this version, the liquid reservoir 232 is created by a single membrane 234 that is sealed around its perimeter 236 against the inside of the top cover 54". The reservoir is filled through a self-sealing fill port 237. The liquid flow path begins at a through-hole 238 and communicates with a channel 240 formed under the top membrane 50" of the top cover 54". The flow of liquid medication then proceeds into the micropump through the valve membrane (not shown in FIG. 17 due to the scale of the drawing, but located between the top cover 54" and the lower valve body 204") and the lower valve body 204" as described previously. The delivery cannula 92' of FIG. 12 is epoxy-bonded into the hub 216" and receives the flow of liquid medication directly from the micropump. As in the embodiment of FIGS. 12–16, the piezoelectric element 36" may be permanently affixed to the top surface of the membrane 50" (thus becoming a part of the disposable portion of the infusion device), or may be temporarily adhered to the membrane 50" only when the disposable and reusable portions of the infusion device are coupled together (thereby becoming a part of the reusable portion as in the embodiment illustrated in FIGS. 1–10 and 11A–11E).

Figure 18:
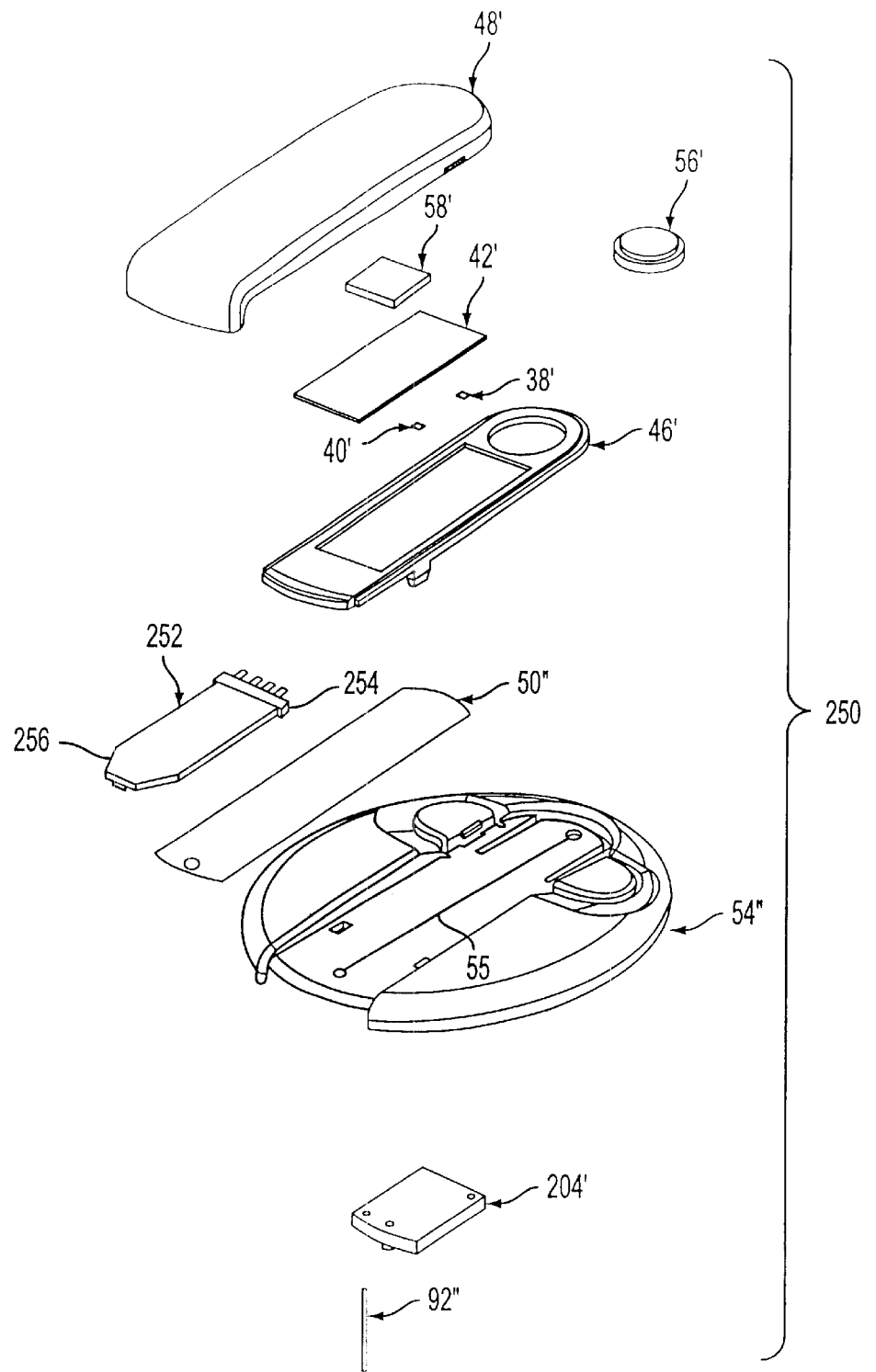
FIG. 18 is an exploded perspective view similar to that of FIG. 12, illustrating certain components of a drug infusion device constructed in accordance with a third embodiment of the present invention.

FIGS. 18 and 19 illustrate a drug infusion device 250 constructed in accordance with a third embodiment of the present invention. This embodiment is similar to the first embodiment of FIGS. 1–10 and 11A–11E in that it relies on the use of a pressurized reservoir for containing the liquid medication and for delivering the liquid medication under pressure through the flow channel 55". The reservoir is not shown in the exploded view of FIG. 18, but it will be understood to be similar to that used in the first embodiment as illustrated in FIG. 4. Also not shown in FIG. 18 (but included in the device 250) are the bottom cover 94, liner 96 and cannula shield 100 of FIG. 4.

The principal difference between the embodiment of FIGS. 1–10 and 11A–11E and the embodiment of FIGS. 18 and 19 is the manner in piezoelectric forces are used to control the flow of the pressurized liquid medication through the flow channel 55". In the embodiment of FIGS. 1–10 and 11A–11E, a simple disk-type piezoelectric element 36 acts as a valve actuator to control the flow of liquid medication in the flow channel 55 via the membrane 50 and channel discontinuity 106 as shown in FIGS. 6 and 7. In the embodiment of FIGS. 18 and 19, a modified valve structure is used and the disk-type piezoelectric element 36 is replaced by a cantilevered piezoelectric actuator 252. The cantilevered piezoelectric actuator 252 is clamped at one end 254 to the underside of the circuit board 42' of the reusable portion, and is left free at its opposite end 256. The resulting structure is capable of greater deflection and greater actuation force at its free end 256 than is possible with a simple disk-type piezoelectric element, allowing for higher operating pressures. During operation of the device 250, the free end 256 of the cantilevered actuator 252 deflects upwardly and downwardly relative to the membrane 50" under the control of the logic controller chip 58'.

FIGS. 19 and 20 are cross-sectional views taken longitudinally through the outlet end of the flow channel 55" of FIG. 18, and illustrate the manner in which the cantilevered piezoelectric actuator 252 controls the flow of liquid medication into the delivery cannula 92". As illustrated, a hole 258 is formed in the membrane 50" in alignment with the bore of the delivery cannula 92'. The proximal end of the delivery cannula 92' extends upwardly through the valve body 204' (which in this embodiment has no valve function and merely acts as a support for the delivery cannula) and the top cover 54", and terminates at a level slightly above the top surface of the membrane 50". An elastomeric disk 260, made of latex rubber or the like, is stretched over the open end of the delivery cannula 92" and is bonded at its periphery to the top surface of the membrane 50". The combination of the elastomeric disk 260 and the surrounding membrane 50" creates a hermetic seal for the liquid flow path. The action of the free end 256 of the cantilevered piezoelectric actuator 252 in pressing the stretched latex disk 260 against the blunt orifice at the top of the delivery cannula 92" produces a valve function. In the condition shown in FIG. 19, in which the cantilevered piezoelectric actuator 252 is not energized, the valve is closed. When the cantilevered piezoelectric actuator 252 is energized, its free end 256 is deflected upwardly and the fluid pressure in the flow channel 55" (due to the pressurized reservoir) causes the latex disk 260 to expand upwardly and separate from the top opening of the delivery cannula 92". The valve is thereby opened, and the liquid medication flows from the channel 55" into the delivery cannula 92". As in the embodiment of FIGS. 1–10 and 11A–11E, the duty cycle of the cantilevered piezoelectric actuator 252 dictates the flow rate of the liquid medication through the flow channel 55" and delivery cannula 92".

Other modes of operation are also possible with the arrangement shown in FIGS. 19 and 20. For example, if the cantilevered piezoelectric actuator 252 is of the type that responds to both positive and negative driving voltages, a constant voltage of suitable plurality may be applied to force the free end 256 of the actuator 252 against the latex disk 250 during periods when it is desired to maintain the valve in a closed position. The voltage can then be reversed to open the valve.

Figure 21:
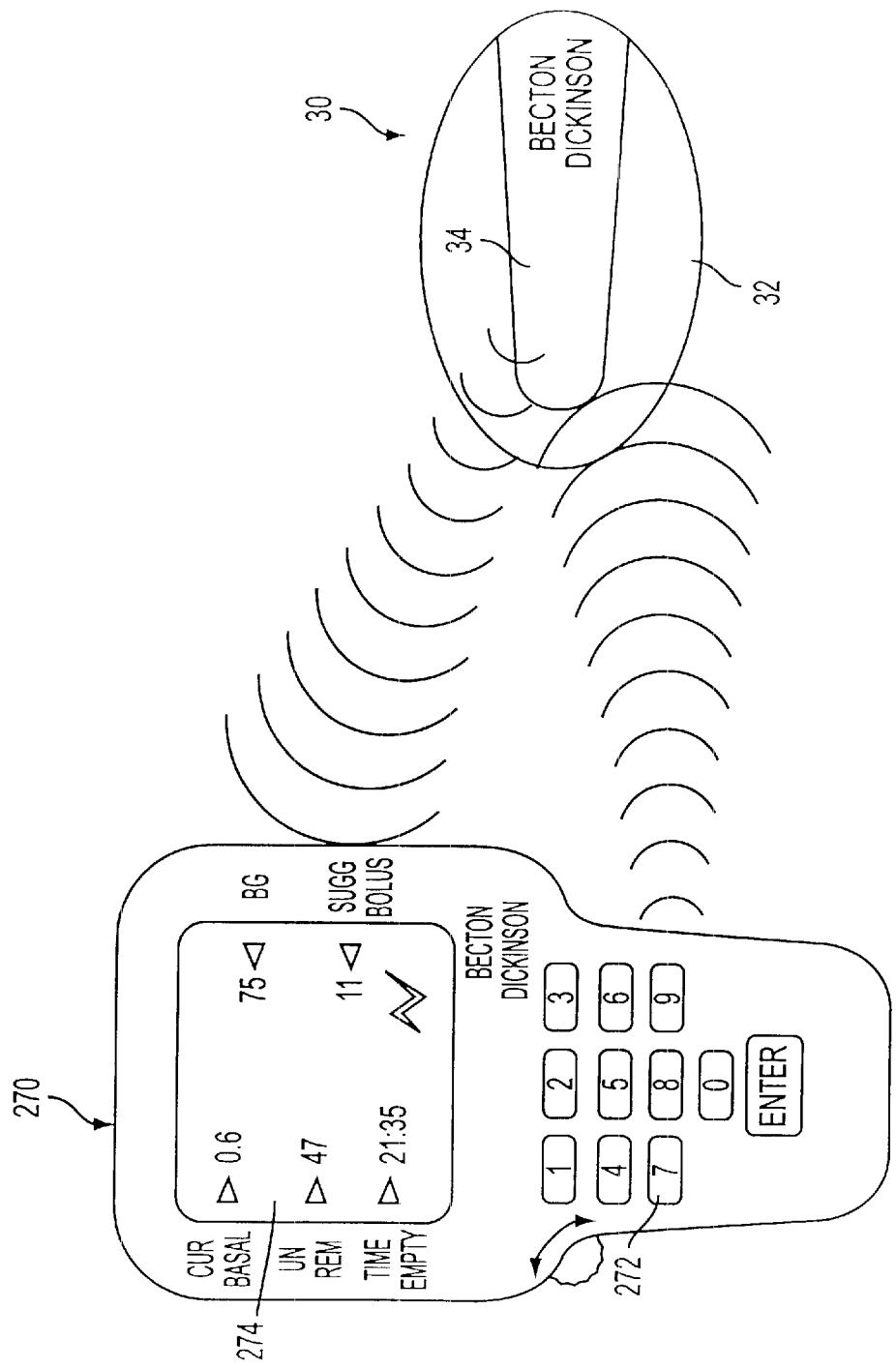
FIG. 21 illustrates a wireless external programming unit that may be used to program the drug infusion device of the present invention.
Figure 22:
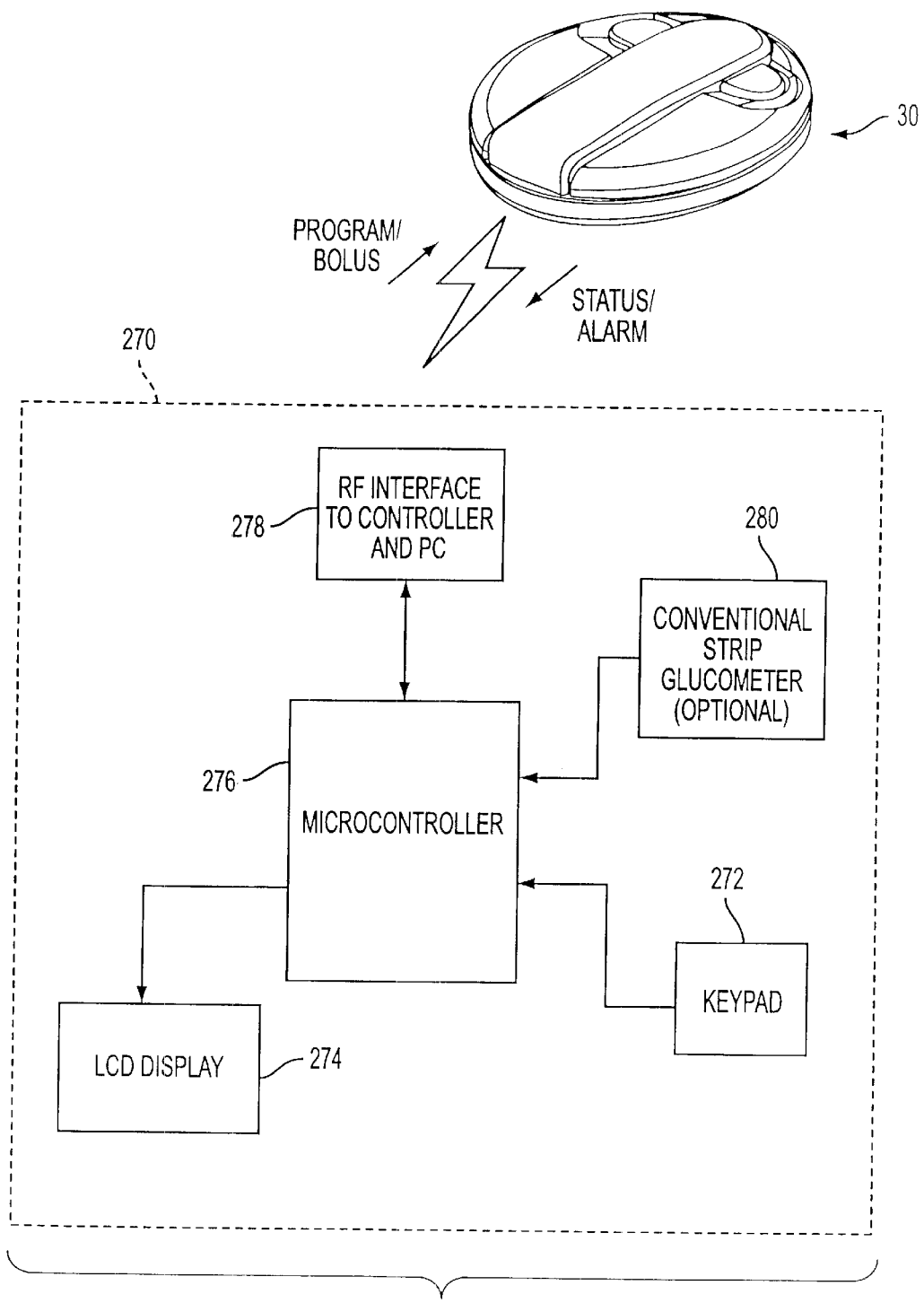
FIG. 22 is a block diagram illustrating the principal electrical components of the wireless external programming unit of FIG. 21.

FIG. 21 illustrates the external configuration of one type of wireless external programming unit 270 which may be used to program the drug infusion device of the present invention. Although the drug infusion device illustrated in FIG. 21 is the device 30 of FIGS. 1–10 and 11A–11E, it will be understood that the programmer 270 may also be used in connection with the embodiment of FIGS. 12–17 and the embodiment of FIGS. 18–20. In the illustrated embodiment, the physical size of the programmer 270 is similar to that of a pocket calculator or personal digital assistant (PDA). As in the case of those devices, the programmer 270 includes a numeric keyboard 272 and LCD-type display screen 274. Assuming that the device 30 is used for insulin infusion, the user can use the programmer 270 to set, change or program the insulin flow rate in accordance with the user's needs. For example, as in the case of commercially available insulin pumps, a basal flow rate in the range of 0.2 units per hour to 5.0 units per hour can be selected. At mealtimes, the programmer 270 can be set to deliver a bolus flow rate of 1.2 milliliters per hour. The display screen 274 provides visual confirmation of the information keyed in by the user and also displays status information concerning the operation of the device 30. Glucose data may also reside in the programmer 270, either as a result of having been electronically transmitted or input to the programmer 270, created in the programmer 270, or keyed into the programmer 270 by the user. The user's carbohydrate intake data may also be keyed into the programmer 270. Based on insulin delivery history and glucose data, the programmer 270 can display suggested bolus doses and/or basal rate changes to the user. The user can accept or reject these suggestions as desired.

The programmer 270 communicates wirelessly with the reusable controller 34 of the drug infusion device 30, such as by radio frequency (RF) or optical infrared (IR) communication methods. These methods are well known in the art and need not be described in detail. RF transmission is advantageous in that it does not require a direct line of sight and can take place through the user's clothing. However, RF transmission introduces certain regulatory issues and is also somewhat more susceptible to interference from stray sources unless precautions (such as digital coding) are taken. IR transmission is less susceptible to interference and poses fewer regulatory difficulties, but it cannot penetrate clothing and requires a direct line of sight between the programmer 270 and the drug infusion device 30. Inductive coupling is another method that can be used to provide wireless communication between the programmer 270 and the infusion device 30. In cases where wireless communication is not needed or desired, a "docking station" configuration can be used and hard-wired communication can take place between the programmer 270 and the infusion device 30 through electrically conductive contacts.

As illustrated in FIG. 21, the communication between the programmer 270 and the drug infusion device 30 is preferably two-way. This allows the programmer 270 to transmit flow rate settings and other commands to the drug infusion device 30, and also allows the drug infusion device 30 to transmit confirmation of these settings and commands back to the programmer 270 to preclude the possibility of erroneous operation due to communication errors. The return communication link also allows the drug infusion unit 30 to transmit status information back to the programmer 270 so that it can be displayed to the user on the display screen 274. Such status information may include the actual flow rate of insulin in the device 30, the time or fluid quantity remaining before the reservoir in the disposable portion 32 becomes empty, overflow or underflow alarms, a low battery condition in the reusable controller 34, and similar types of information.

FIG. 21 is a block diagram which illustrates the principal electrical components of the programmer 270 of FIG. 20. These components include the keypad 272 and LCD display 274 discussed previously, a microcontroller 276 for controlling the operation of the programmer 270, and an RF (or, if desired, IR) interface 278 for communicating with the logic controller 58 of FIG. 10. The interface 278 can also provide wireless communication with an external personal computer (PC), allowing the user to download and/or upload insulin delivery schedules, glucose data, carbohydrate data, and software programs. Optionally, the programmer 270 may also include (or may be connected to) a conventional strip glucometer 280 for obtaining blood glucose data from the user and applying the data as an input to the microcontroller 276 for display and/or further processing. With direct inputs of the user's blood glucose levels, the programmer 270 and infusion device 30 can operate in a "closed loop" mode that automatically adjusts the flow rate of insulin as needed to maintain the user's blood glucose levels within fixed limits.

The configuration and design of the programmer 270 can take a number of different forms. Functionally, it may serve only as a programmer for the drug infusion device 30, or it may serve as both a programmer and an integral blood glucose meter as discussed above. In the latter case, the programmer 270 can be packaged with a lancet device for the convenience of the user. The programmer 270 can also be designed for use with a docking station so that it can communicate with the user's desktop or laptop computer via a hard-wired connection. Alternatively, the same RF or IR communication link that is used to communicate with the drug infusion device 30 can also be used to communicate with the user's computer, if the user's computer is suitably equipped. The programmer 270 can, if desired, be reduced in size so that it can be carried in a pocket or on a belt clip, similar to the manner in which a pager is carried. Further reductions in size to credit card, wallet, key fob and wrist watch configurations are possible.

In addition to the basic functions that are required to control and monitor the drug infusion device 30, the wireless programmer 270 may be provided with related capabilities that are helpful to the user. For example, the programmer 270 can store alarm records or blood glucose data that has been manually entered by the user. The programmer 270 can also be designed to assist the user with carbohydrate counting, meal averaging, pattern management, insulin dose calculations and recommendations, advice for dealing with low or elevated blood glucose levels, and so on. The programmer 270 can also incorporate a time-of-day clock, calendar, scheduler and other functions normally associated with a personal digital assistant (PDA).

In lieu of providing a dedicated programmer 270, the functions of the programmer 270 may be carried out by a commercially available PDA. Examples of suitable PDAs include the Palm Pilot™ PDA that is available from 3Com Corporation of Santa Clara, Calif., and the Visor™ PDA that is available from Handspring of Mountain View, Calif. General-purpose IR interfaces and related software programs arc already available from these vendors (as well as from aftermarket sources) and can be used to establish two-way communication between the PDA and the drug infusion device 30. Alternatively, if RF communication is desired, a dedicated RF module can be designed that can be plugged into an existing PDA. An advantage of using an off-the-shelf PDA as the programmer 270 is that many different types of software modules and hardware accessories already exist for these types of devices. Although intended for general use, these modules and accessories can be adapted to the requirements of the present invention. From the user's standpoint, the use of a PDA is advantageous because it can serve not only as a programmer 270 for the drug infusion device 30, but also as a general-purpose digital assistant.

Although a wireless programmer 270 is preferred for use in the present invention, this is not essential. In some situations, it may be preferable to employ a programmer 270 which is connected to the drug infusion device 30 by means of a hard-wired link, such as the docking port arrangement mentioned earlier. The hard-wired link may be temporary or permanent, and would have the advantage of virtually eliminating any possibility of interference in the communication between the programmer 270 and the drug infusion device 30. It will also be appreciated that, in some implementations of the present invention, the programmer 270 may be eliminated entirely and some or all of its functions incorporated into the reusable portion 34 of the drug infusion device 30.

Although the present invention has been described in reference to certain preferred embodiments thereof, it will be understood that the invention is not limited to the details of these embodiments. Various substitutions and modifications have been described in the course of the foregoing description, and others are possible. For example, an integral blood glucose meter may be incorporated into the disposable portion of the infusion device 30. Also, by reversing the direction of liquid flow within the disposable portion 32, the device 30 may be used for sampling or monitoring of blood analytes rather than for infusion of liquid medications. Other substitutions and modifications will occur to those of ordinary skill in the art. All such substitutions and modifications are intended to fall within the scope of the invention as defined in the appended claims.

What is claimed is:

1. A wearable self-contained device for delivering a liquid medication by continuous infusion into a patient, comprising:

a disposable portion comprising a housing, a reservoir in said housing for containing a supply of said liquid medication and for delivering said liquid medication under pressure wherein said reservoir comprises at least one Belleville spring element for pressurizing the liquid medication contained in said reservoir, a delivery cannula carried by said housing, and a flow channel for conducting said liquid medication from said reservoir to said delivery cannula;

a reusable portion removably connected to said disposable portion, said reusable portion comprising a closed loop control circuit for maintaining a predetermined flow of said liquid medication through said flow channel;

a flow control valve in at least one of said disposable and reusable portions for controlling the flow of said liquid medication through said flow channel from said reservoir to said delivery cannula;

an actuator in at least one of said disposable and reusable portions for actuating said flow control valve, said actuator being electrically connectable to said closed loop control circuit; and a flow sensor in at least one of said disposable and reusable portions for sensing the flow of said liquid medication through said flow channel, said flow sensor being electrically connectable to said closed loop control circuit.

2. A device as claimed in claim 1, wherein said flow control valve comprises a fixed obstruction in said flow channel and a flexible membrane that is held in contact with said obstruction by said actuator to prevent liquid flow through said flow channel except when said actuator is energized by said control circuit.

3. A device as claimed in claim 2, wherein said actuator comprises a piezoelectric element which, when energized by said control circuit, flexes to allow said membrane to separate from said obstruction so that said liquid medication can flow through said flow channel.

4. A device as claimed in claim 3, wherein said piezoelectric element is energized in a pulsatile manner by said control circuit, so that said flow control valve is repeatedly opened and closed with a duty cycle that maintain said predetermined flow of said liquid medication through said flow channel.

5. A device as claimed in claim 1, wherein said flow sensor comprises a thermal emitter and a thermal detector in thermal contact with the liquid medication flowing in said flow channel, said thermal emitter being located upstream of said thermal detector relative to the direction of liquid flow in said flow channel.

6. A device as claimed in claim 1, wherein at least one wall of said flow channel comprises a flexible membrane which forms an exposed face of said disposable portion that is brought into contact with said reusable portion when said disposable and reusable portions are connected together, and wherein said actuator and said flow sensor are contained in said reusable portion and operate through said flexible membrane of said disposable portion so that said flow channel can remain sealed when said reusable portion is disconnected from said disposable portion.

7. A wearable, self-contained device for delivering a liquid medication by continuous infusion into a patient, comprising:

a disposable portion comprising a housing, a reservoir in said housing for containing a supply of said liquid medication, a deli very cannula carried by said housing, and a flow channel for conducting said liquid medication from said reservoir to said delivery cannula;

a reusable portion removably connected to said disposable portion, said reusable portion comprising a closed loop control circuit for maintaining a predetermined flow of said liquid medication through said flow channel;

a pump in at least one of said disposable and reusable portions for pumping said liquid medication through said flow channel from said reservoir to said delivery cannula, said pump being electrically connectable to said closed loop control circuit; and a flow sensor in at least one of said disposable and reusable portions for sensing the flow of said liquid medication through said flow channel, said flow sensor being electrically connectable to said closed loop control circuit wherein said flow sensor comprises a thermal emitter and a thermal detector in thermal contact with the liquid medication flowing in said flow channel, said thermal emitter being located upstream of said thermal detector relative to the direction of liquid flow in said flow channel.

8. A device as claimed in claim 7, wherein said pump comprises a diaphragm pump in said disposable portion that is driven by an actuator in at least one of said disposable and reusable portion.

9. A device as claimed in claim 8, wherein said actuator comprises a piezoelectric element.

10. A device as claimed in claim 9, wherein said piezoelectric element comprises a cantilevered piezoelectric element.

11. A device as claimed in claim 8, wherein said diaphragm pump comprises at least one check valve for restricting liquid flow to a single direction.

12. A device as claimed in claim 7 wherein at least one wall of said flow channel comprises a flexible membrane which forms an exposed face of said disposable portion that is brought into contact with said reusable portion when said disposable and reusable portions are connected together, and wherein said flow sensor is contained in said reusable portion and operates through said flexible membrane of said disposable portion so that said flow channel can remain sealed when said reusable portion is disconnected from said disposable portion.

13. A system for delivering a liquid medication by continuous infusion into the skin of a patient, comprising:

a disposable portion comprising a housing, a reservoir in said housing for containing a supply of said liquid medication wherein said reservoir comprises at least one Belleville spring element for pressurizing the liquid medication contained in said reservoir, a delivery cannula carried by said housing, and a flow channel for conducting said liquid medication from said reservoir to said delivery cannula;

a reusable portion removably connected to said disposable portion, said reusable portion containing electrical flow control circuitry for controlling the flow of said liquid medication in said flow channel in response to wireless control signs, said reusable and disposable portions when connected to each other constituting a wearable, self-contained infusion device; and a wireless unit separate from said reusable and disposable portions for transmitting wireless control signals to said reusable portion to control the flow of said liquid medication in said flow channel of said disposable portion.

14. A system as claimed in claim 13, wherein said wireless unit transmits radio frequency control signals to said reusable portion.

15. A system as claimed in claim 13, wherein said wireless unit transmits optical control signals to said reusable portion.

16. A system as claimed in claim 13, wherein said wireless unit includes a keypad and a display device.

17. A system as claimed in claim 13, wherein said wireless unit receives and displays status information transmitted by said reusable portion.

18. A system as claimed in claim 17, wherein said status information is selected from the group consisting of a flow rate of said liquid medication, an amount of time remaining until said reservoir becomes empty, a quantity of liquid medication remaining in said reservoir, a warning of an incorrect flow rate of said liquid medication, and an indication of a battery condition in said reusable portion.

* * * * *